US012708300B2

(12) United States Patent
Shi et al.

(10) Patent No.: US 12,708,300 B2
(45) Date of Patent: Aug. 18, 2026

(54) LANCING DEVICE UTILIZING TAIL HANDLE TO LOAD AND ADJUST DEPTH

(71) Applicant: STERILANCE MEDICAL (SUZHOU) INC., Suzhou (CN)

(72) Inventors: Guoping Shi, Suzhou (CN); Xiangsheng Wang, Suzhou (CN); Jinquan Zhang, Suzhou (CN)

(73) Assignee: STERILANCE MEDICAL (SUZHOU) INC., Suzhou (CN)

( * ) Notice: Subject to any disclaimer, the term of this patent is extended or adjusted under 35 U.S.C. 154(b) by 972 days.

(21) Appl. No.: 18/037,356

(22) PCT Filed: Apr. 21, 2021

(86) PCT No.: PCT/CN2021/088758
§ 371 (c)(1),
(2) Date: May 17, 2023

(87) PCT Pub. No.: WO2021/213447
PCT Pub. Date: Oct. 28, 2021

(65) Prior Publication Data

US 2023/0309879 A1 Oct. 5, 2023

(30) Foreign Application Priority Data

Apr. 21, 2020 (CN) ........................ 202010315956.6

(51) Int. Cl.
*A61B 5/151* (2006.01)
*A61B 5/15* (2006.01)

(52) U.S. Cl.
CPC ...... *A61B 5/15188* (2013.01); *A61B 5/15019* (2013.01); *A61B 5/15105* (2013.01); *A61B 2560/0418* (2013.01)

(58) Field of Classification Search
CPC .......... A61B 5/15188; A61B 5/150022; A61B 5/15019; A61B 5/15105; A61B 5/150198; A61B 5/150541; A61B 5/15111; A61B 5/15117; A61B 5/1519; A61B 5/15196; A61B 5/150007; A61B 5/150206; A61B 5/150763; A61B 5/15
See application file for complete search history.

(56) References Cited

U.S. PATENT DOCUMENTS 5,984,940 A * 11/1999 Davis .............. A61B 5/150198 606/181
2009/0036916 A1* 2/2009 Fukuzawa ........... A61B 5/1519 606/182
2010/0241149 A1* 9/2010 Nishiyama ....... A61B 5/150412 606/181

* cited by examiner

*Primary Examiner* — Brigid K Byrd
(74) *Attorney, Agent, or Firm* — Oliff PLC

(57) ABSTRACT

A lancing device utilizing tail handle to load and adjust depth, includes a shell, an ejection pin, and a tail handle. The tail handle rotates fit with shell in circumferential direction of lancing device and slides fit with shell in axial direction of lancing device; the tail handle has forward sliding limit relative to shell in axial direction; passive impact surface is arranged corresponding to active impact surface on ejection pin for adjusting puncture depth and loading, and passive impact surface is formed by spiral action surface on tail handle; in use state, rotating tail handle will drive position of impact point on passive impact surface to change in axial direction of lancing device, thereby adjusting lancet tip puncture depth; pulling the tail handle backward will force the passive impact surface to come into contact with the active impact surface, and drive the ejection pin to be loaded and locked.

9 Claims, 18 Drawing Sheets

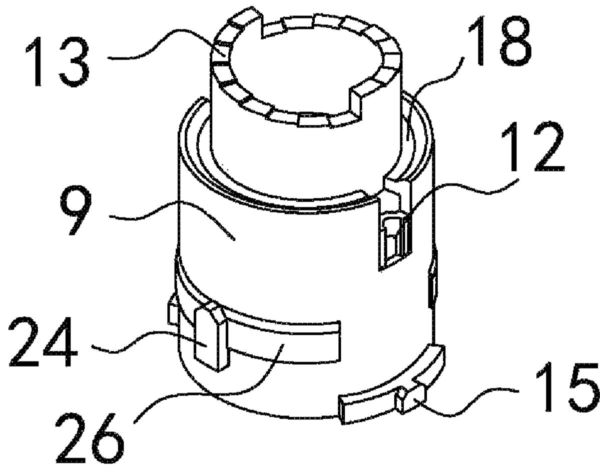
Fig. 8
13
12
9
26
24
15
15
Fig. 9
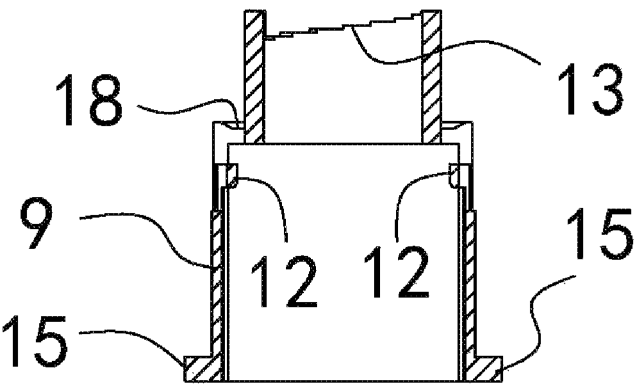
Fig. 10

22
10
19
4
29
14
30
15
17
23
6
1
3
27
7
13
12
11
20
2
31

22
27
10
7
29
13
14
12
30
11
15
20
17
23
6
2
5
31
1

22
10
19
4
29
14
30
15
17
23
5
1
3
31
2
6
20
11
12
13
7
27

22
10
29
14
30
15
17
23
1
5
3
31
2
6
20
11
12
13
7
27

LANCING DEVICE UTILIZING TAIL HANDLE TO LOAD AND ADJUST DEPTH

FIELD OF THE INVENTION

The present invention relates to medical blood collection instruments, in particular to a lancing device used in conjunction with a disposable lancet. This lancing device is able to directly utilize a tail handle to load and adjust the puncture depth, with one click multi-purpose, easily identified, and conveniently operated.

BACKGROUND ART

Lancing device is a kind of blood collection instrument used in conjunction with disposable lancet, the lancing device able to be reused, while the lancet only used once to avoid cross infection. The development of lancing device has a history of decades, with the improvement of lancing device through many stages, and now lancing device is gradually becoming mature, but in the development of lancing device, how to improve convenience of operation and user experience of lancing device have always been the concern of those skilled in the field.

On Jan. 21, 2015, Chinese patent CN204106018U issued a utility model patent (hereinafter referred to as "comparison document 1") with patent number 201420573995.6, titled "lancing device with firing mechanism at level of lancing device shell". The patent is equipped with a puncture depth adjustment device at the tail of the lancing device (see distance adjustment mechanism 60 in FIGS. 1-3 of comparison document 1), a triggering device (see firing mechanism 30 in FIGS. 1-3 of comparison document 1), and a needle unloading device (see needle withdrawal mechanism 50 in FIGS. 1-3 of comparison document 1) on the side of the lancing device. The patent is limited by the tail puncture depth adjustment device under analysis and research, so it does not have the ability to use the knob 62 at the tail of the lancing device (belonging to the operating part of the distance adjustment mechanism 60) to carry out the secondary loading operation on the shooting rod (referred to as pin holder 20 in comparison document 1). At the same time, it should be noted that there is no other structure on the lancing device except for knob 62 that can be used to operate the shooting rod for secondary loading. This will bring a problem in use, that is, the user installs the needle and pushes the lancet to complete the loading and firing, once it is found that there is no puncture to the skin or the puncture depth is not enough, due to the lack of a second loading opportunity, the launched lancet can only be removed, replaced by a new lancet and the puncture depth device adjusted to the appropriate position, and then fire again for blood collection. This will inevitably result in waste of the previous lancet.

To solve the above issue, a device or structure should be designed on the lancing device that can provide secondary loading operation.

On Jan. 30, 2018, Chinese patent CN107638180A issued an invention patent application (hereinafter referred to as "comparison document 2") with application number 201710991669.5, titled "A lancing device using a tail handle for loading and unloading needles". The patent is equipped with a puncture depth adjustment device at the rear of the lancing device (see manual adjustment ring 10 in FIG. 1 of comparison document 2), and a secondary loading operation device at the rear of the lancing device (see tail handle 22 in FIG. 1 of comparison document 2). Although the comparison document 2 solves the problem of the inability to perform secondary loading operation in the comparison document 1, the overall structural design of the comparison document 2 adopts the technical concept of setting a manual adjustment ring at the rear of the lancing device and designing a corresponding puncture depth adjustment mechanism inside the lancing device to meet the requirements of puncture depth adjustment, at the same time, a tail handle is installed at the tail of the lancing device and a corresponding secondary loading mechanism is designed inside the lancing device to meet the requirements of secondary loading.

In short, the two belong to two sets of mechanisms, which are relatively independent in structure and do not interfere with each other. Therefore, the shortcomings are that there are many components, complex structures, difficult processes, and high manufacturing costs.

Therefore, how to improve the existing design of the comparison document 2 mentioned above, so that it can be used with multiple buttons, reduce the number of components, simplify the structure, and facilitate identification and operation, is a problem that the present invention needs to solve.

CONTENT OF THE INVENTION

This invention provides a lancing device utilizing tail handle to load and adjust depth, which is aiming at achieving one key multi-purpose, simplifying the structure, facilitating recognition and operation, and thus solve the problem pointed out in the background art in the structural design of the existing lancing device (especially the comparison document 2).

To achieve the above purpose, the technical scheme adopted by the present invention is: A lancing device utilizing tail handle to load and adjust depth, includes a shell, an ejection pin, and a tail handle.

The shell is a pen shell structure of lancing device, an ejection chamber is arranged inside the shell, and a lancing end face is provided at the front end of the shell;

The ejection pin is an ejection component capable of installing a lancet, the ejection pin is located in the ejection chamber, a loading locking and unlocking structure is arranged between the ejection pin and the shell, an active impact surface is set at the rear of the ejection pin to adjust puncture depth, and the active impact surface is facing towards the front of the lancing device;

The tail handle is a handle set at the tail of the lancing device to drive the ejection pin to be loaded.

Its innovation lies in: The tail handle is sleeved and connected relative to the shell, the tail handle rotates fit with the shell in a circumferential direction of the lancing device, and at the same time, the tail handle slides fit with the shell in an axial direction of the lancing device.

Between the tail handle and the shell, one is equipped with an axial limit surface, the other is equipped with a limit action part, and the axial limit surface contacts fit with the limit action part to limit the position of the tail handle relative to the shell to slide forward in an axial direction.

A passive impact surface is arranged corresponding to the active impact surface for both adjusting puncture depth and loading, the passive impact surface is directly or indirectly formed by a spiral action surface on the tail handle, rotating the tail handle is able to change the position of impact point on the passive impact surface in the axial direction of the lancing device.

In use state, when the tail handle is rotated, the tail handle drives the position of the impact point on the passive impact surface to change in the axial direction of the lancing device, thereby changing the distance between the lancing end face and the impact point on the passive impact surface in the axial direction of the lancing device, hereby adjusting the lancet tip puncture depth accordingly; When the tail handle is pulled backward, the tail handle forces the passive impact surface to contact the active impact surface at the rear of the ejection pin, and drives the ejection pin to move backward relative to the shell, until the ejection pin is loaded and locked.

Relevant content of the present invention is explained as follows:

1. In the present invention, the meaning of “front” in “forward”, “front end”, “the front of” refers to the direction indicated by the tip of lancing device or the shooting direction of lancet. The meaning of “back” in “backward”, “the rear of” refers to the direction indicated by the tail of the lancing device or the opposite direction of shooting direction of lancet.

2. In the present invention, the “axis” refers to the axis direction of lancing device, which is also the ray direction of the line connecting the tip and tail of lancing device, or the front and back direction. The “circumferential direction” refers to the circumferential direction of lancing device.

3. In the present invention, the meaning of “outer” in terms of “outer edge”, “exposed”, and “outer side” is relative to “inner”. The ‘outer edge’ is opposite to the ‘inner edge’. The ‘outer’ is opposite to the ‘inner’. ‘Exposed’ refers to being exposed on the outside 4. In the above technical scheme of the present invention, “the passive impact surface is directly or indirectly formed by a spiral action surface on the tail handle”, it has one of the following two meanings:

The first situation is: the passive impact surface is directly formed by a spiral action surface on the tail handle:

A sleeve structure is arranged on the tail handle, the sleeve structure is provided with an inner end face which is facing towards the rear of the lancing device, and the spiral action surface is a spiral step surface or a spiral surface or an inclined surface, the spiral step surface or spiral surface or inclined surface is directly arranged on the inner end face of the sleeve structure of the tail handle.

The second situation is: the passive impact surface is indirectly formed by a spiral action surface on the tail handle, specifically:

A sliding sleeve is provided for the tail handle, the sliding sleeve is positioning connected relative to the shell in circumferential direction of the lancing device, and sliding connected in axial direction of the lancing device at the same time. The tail handle is connected to the sliding sleeve through a screw pair, constituting a sliding sleeve axial movement mechanism which is adjusted by the rotation of the tail handle. The passive impact surface is the inner end face of the sliding sleeve, and the spiral action surface is a screw pair (Essentially, the screw pair plays the same role as the spiral action surface, or rather, the screw pair acts as a spiral to change the passive impact surface).

The screw pair is formed by the cooperation of a spiral groove and a driving block; between the spiral groove and the driving block, one is located on the tail handle, and the other is located on the sliding sleeve. The screw pair may be formed by the cooperation of external thread and internal thread; between the external thread and the internal thread, one is located on the tail handle, and the other is located on the sliding sleeve.

The design principle and technical concept of the present invention are: In order to achieve one key multi-purpose, simplify the structure, and facilitate identification and operation, the present invention is aiming to replace the tail handle that was originally only used for loading and the manual adjustment ring that was originally only used for adjusting the puncture depth (making depth adjustment structure at the rear, which means that the depth adjustment is designed at the back of lancing device). These two independent and non-interference functional components are combined, to simplify the structure and facilitate identification and operation. To achieve this goal, the technical concept adopted by the present invention mainly includes: The passive impact surface which was specifically used to adjust the puncture depth in the original depth adjustment structure at the rear is directly or indirectly arranged at the tail handle which was specifically used for loading. This modification is not a simple replacement, but rather requires direct or indirect grafting through the spiral action surface. At the same time, it is necessary to improve the connection relationship between the tail handle and the shell, that is, the tail handle was originally connected in axial sliding relative to the shell and in circumferential positioning. The improved tail handle is connected in axial sliding relative to the shell, while also being connected in circumferential rotation. In this way, for the same tail handle, when manually rotating the tail handle, the position of the passive impact surface in the axial direction of the lancing device can be changed through the spiral action surface, thereby adjusting the puncture depth. When the tail handle is pulled back, the initial impact surface can be used as a loading pulling surface, and after contact with the active impact surface, the ejection pin will be driven to load. From the above, it can be seen that the outstanding contribution of the tail handle in the present invention is that it is endowed with three attributes at the same time. Firstly, the passive impact surface serves as the limiting surface for puncture in controlling puncture depth, secondly, the passive impact surface serves as the spiral action surface (spiral adjustment surface) for adjusting puncture depth in controlling the puncture depth, and thirdly, the passive impact surface serves as a loading pulling surface for the loading of ejection pin. From the perspective of existing technology, in the past, the motion relationship required to adjust the puncture depth was rotation, while the motion relationship required for loading was axial sliding, and the two cannot interfere with each other. The reason why comparison document 2 can simultaneously use the tail handle for loading and unloading lancets is that both loading and unloading lancets slide axially. The present invention breaks the limitations of traditional structural design in the past and provides a novel and reasonable structural design. Its technical concept is unique and ingenious, with prominent substantive features and significant progress.

Due to the application of the above scheme, the present invention has the following advantages and effects compared to existing technologies:

1. The present invention enables the tail handle to have two different functions: loading and adjusting the puncture depth, achieving two different functions. Due to the versatility of one key, compared to the existing technology (comparison document 2), it not only reduces the number of parts, but also reduces mold and manufacturing costs.

2. The present invention not only simplifies the product structure design, but also brings positive effects for easy identification and operation.

3. The present invention has good processability, reliable operation, and convenient use, further improving the operational performance of lancing device, and playing a positive role in the improvement and development of lancing device.

DESCRIPTION OF DRAWINGS

FIG. 8 is a first perspective three-dimensional view of the loading adjustment inner sleeve of Embodiment 1 of the lancing device of the present invention;

FIG. 9 is a second perspective three-dimensional view of the loading adjustment inner sleeve of Embodiment 1 of the lancing device of the present invention;

FIG. 10 is a cross-sectional view of the inner sleeve of the loading adjustment inner sleeve of Embodiment 1 of the lancing device of the present invention;

Figure 1:
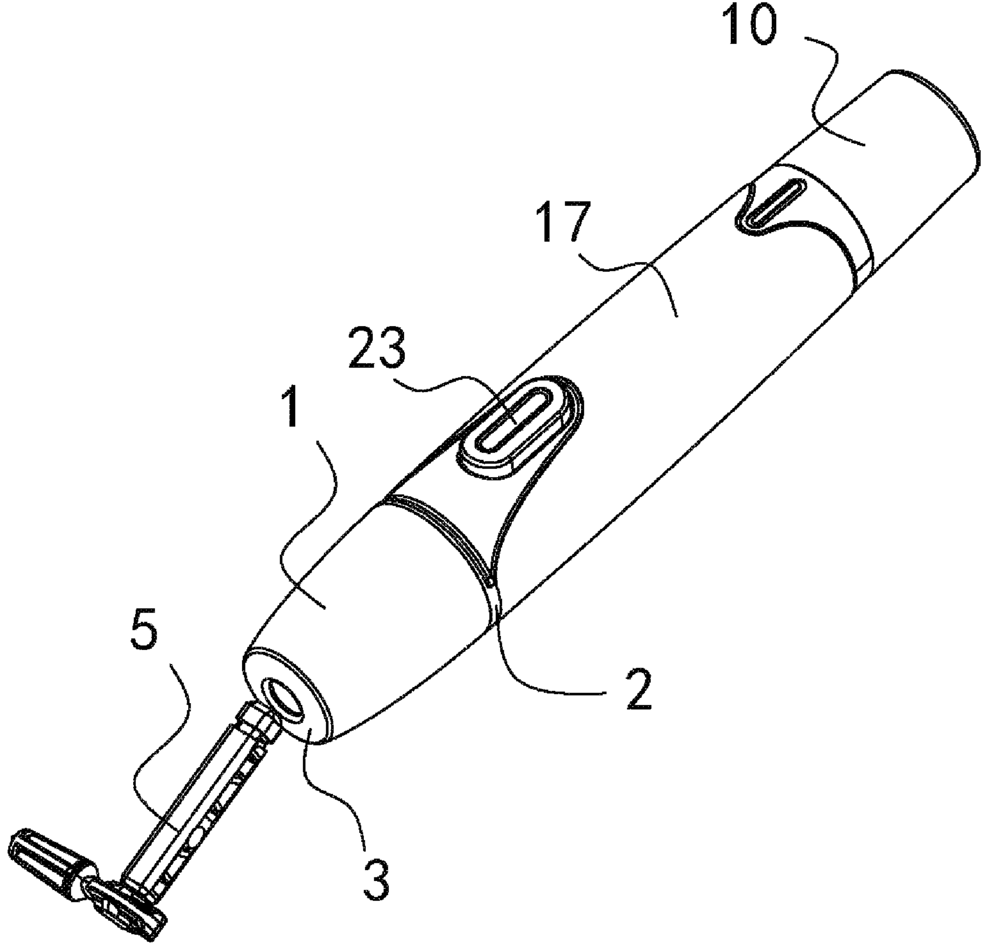
FIG. 1 is a three-dimensional view of Embodiment 1 of the lancing device of the present invention.

In the above figures: 1. cap; 2. middle sleeve; 3. lancing end face; 4. axial limit surface; 5. lancet; 6. ejection pin; 7. active impact surface; 8. outer sleeve; 9. inner sleeve; 10. tail handle; 11. rotating positioning groove; 12. rotating positioning block; 13. passive impact surface; 14. guide slot; 15. guide protrusion; 16. rear end face; 17. housing; 18. front end face; 19. limit action part; 20. rotating limit convex rib; 21. corner limit surface; 22. unloading push handle; 23. button; 24. positioning boss; 25. positioning groove; 26. positioning convex rib; 27. lancet unloading rod; 28. positioning snap; 29. return spring; 30. launch spring; 31. lancet holder; 32. guide rib; 33. driving block; 34. sliding sleeve; 35. spiral groove; 36. guide groove.

MODE OF CARRYING OUT THE INVENTION

The following is a further description of the present invention in conjunction with the accompanying drawings and embodiments.

Embodiment 1: A Lancing Device Utilizing Tail Handle to Load and Adjust Depth As shown in FIGS. 1 to 18, the lancing device comprises a cap 1, a middle sleeve 2, an ejection pin 6, a lancet unloading rod 27, a housing 17, a button 23, a launch spring 30, a return spring 29, an inner sleeve 9, an outer sleeve 8, and a unloading push handle 22 (see FIG. 2). The cap 1, the middle sleeve 2, and the housing 17 are connected to form the shell in the present invention, and there is an ejection chamber inside the shell. The inner sleeve 9 and the outer sleeve 8 are connected to form the tail handle 10 in the present invention. The inner sleeve 9 and the outer sleeve 8 are connected to form the tail handle 10 in the present invention.

Figure 2:
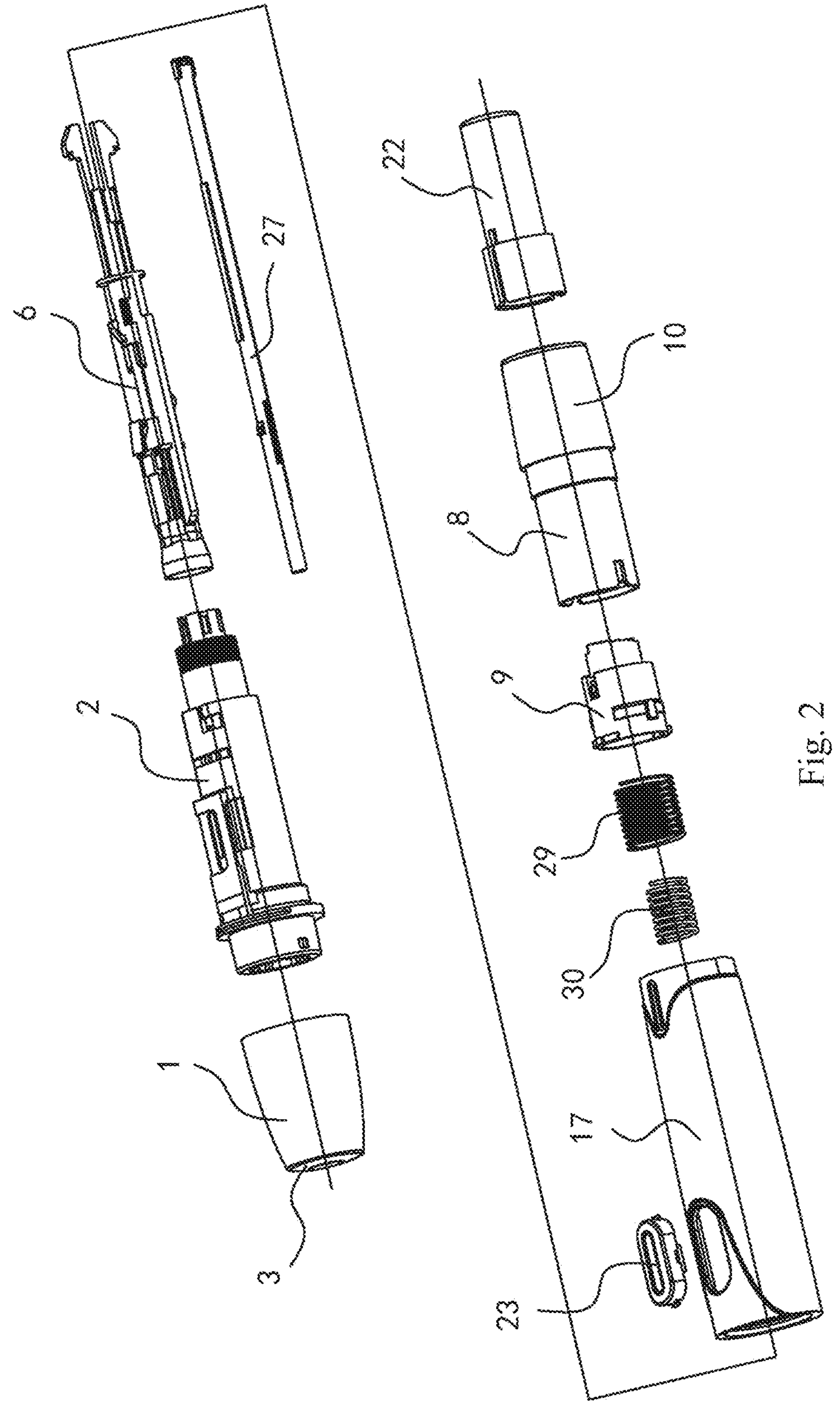
FIG. 2 is a three-dimensional exploded view of Embodiment 1 of the lancing device of the present invention.
Figure 3:
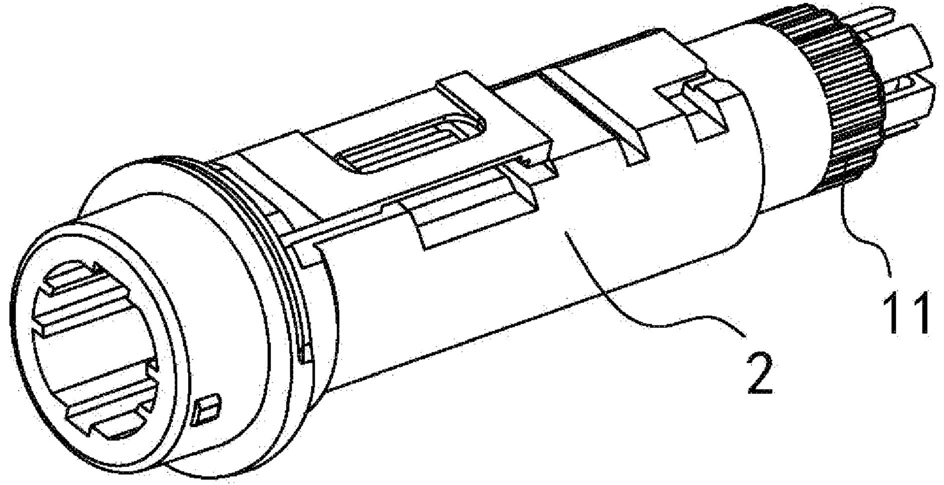
FIG. 3 is a three-dimensional view of middle sleeve of Embodiment 1 of the lancing device of the present invention.
Figure 4:
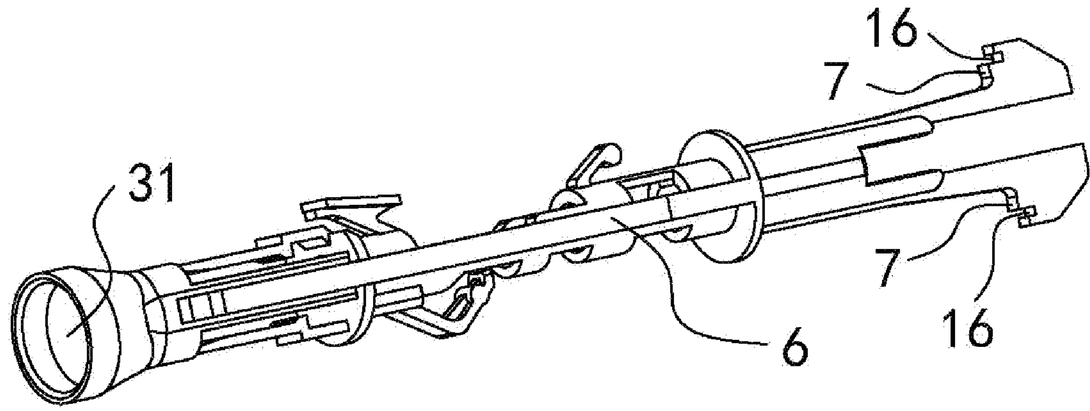
FIG. 4 is a three-dimensional view of ejection pin of Embodiment 1 of the lancing device of the present invention.
Figure 5:
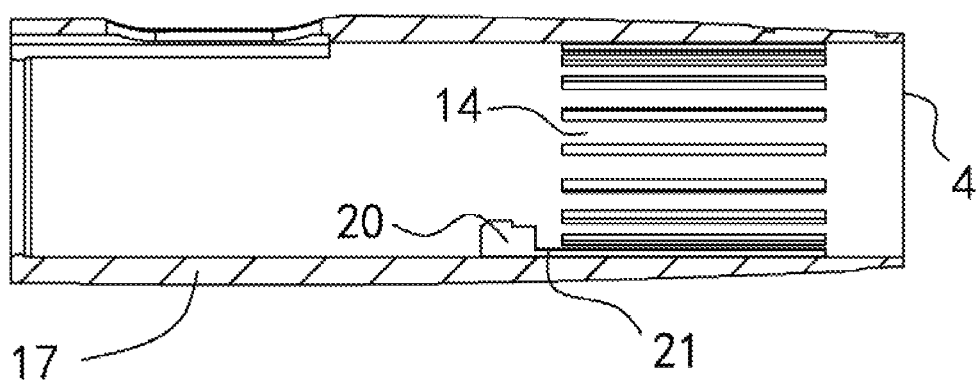
FIG. 5 is a cross-sectional view of the housing of Embodiment 1 of the lancing device of the present invention.

The cap 1 is a sleeve-type cap on the head of lancing device, and the front end of the cap 1 is equipped with a lancing end face 3 for contacting the blood collection position of the human body (see FIG. 1 and FIG. 2). The middle sleeve 2 is a seat body at the front of the lancing device that is used to connect fit with the cap 1. The cap 1 and the middle sleeve 2 are connected through a connection port (see FIG. 2), and the cap 1 and the middle sleeve 2 form a plug-unplug connection through the plug port. The ejection pin 6 is an ejection component capable of installing a lancet 5. The ejection pin 6 is located in the ejection chamber, and a loading locking and unlocking structure is arranged between the ejection pin 6 and the shell. In this embodiment, the head of the ejection pin 6 is equipped with a lancet holder 31 (see FIG. 4) for installing the lancet 5. The housing 17 and the middle sleeve 2 are fixedly connected, but the housing 17 and the middle sleeve 2 may also be designed as an integrated forming structure. The launch spring 30 is a spring that provides puncture power for blood collection, and the launch spring 30 is located in the ejection chamber. The tail handle 10 is a handle set at the tail of the lancing device to drive the ejection pin 6 to be loaded and adjust the puncture depth. The main body of the tail handle 10 is a sleeve structure, which slides and connects in the axial direction of the lancing device relative to the shell. In this embodiment, the sleeve structure of the main body of the tail handle 10 is composed of an inner sleeve 9 and an outer sleeve 8 fixedly connected. The return spring 29 is a spring that provides a reset power of the tail handle 10. The return spring 29 is located in the ejection chamber and acts on the reset direction of the tail handle 10. The lancet unloading rod 27 and unloading push handle 22 are the top rods used to remove the lancet 5 on the lancing device (see FIG. 2).

The innovative content of the present invention is described as follows: The tail handle 10 is connected to the housing 17 in a set (see FIG. 14 and FIG. 15), and the tail handle 10 rotates and fits in a circumferential direction of the lancing device relative to the shell, while the tail handle 10 slides fit in the axial direction of the lancing device relative to the shell. However, in order to ensure that the puncture depth will not be changed during the backward pulling process of the tail handle 10, a composite fit section is needed to be designed between the outer edge of the tail handle 10 and the inner edge of the housing 17. On this composite fit section, between the outer edge of the tail handle 10 and the inner edge of the housing 17, one is provided with a guide slot 14, and the other is provided with a guide protrusion 15. In this embodiment, the guide slot 14 is located on the inner edge of the housing 17 (see FIG. 5-7), while the guide protrusion 15 is located on the outer edge of the tail handle 10 (see FIGS. 12 and 13). The length direction of the guide slot 14 is parallel to the axis of the lancing device, and each guide slot 14 is arranged at intervals in the circumferential direction of the lancing device (see FIG. 5-7).

On the composite fit section, the guide protrusion 15 and the guide slot 14 have two working states. non-cooperative working and cooperative working. In a non-cooperative working state, the guide protrusion 15 and the guide slot 14 are arranged in a staggered position in the axial direction of the lancing device, and the tail handle 10 rotates and fits in the circumferential direction of the lancing device relative to the shell. This is the key technical content of the present invention and the core of achieving its objectives. The present invention utilizes the non-cooperative working state of the guide protrusion 15 and the guide slot 14 to meet the need for circumferential rotation of the tail handle 10 relative to the housing 17 when adjusting the puncture depth, and the cooperative working state to meet the need for axial sliding of the tail handle 10 relative to the housing 17 when the ejection pin 6 is loaded, so that the same tail handle 10 can be used to adjust the puncture depth and drive the ejection pin 6 to be loaded.

On the present invention, the puncture depth adjustment structure adopts a rear adjustment structure (relative to the front or head adjustment structure of the puncture depth), that is, the puncture depth adjustment structure is set at the rear of the lancing device. Due to the fact that the tail handle 10 serves not only as a component to drive the ejection pin 6 to be loaded, but also as a component to adjust the puncture depth. Therefore, starting from the need for rear puncture depth adjustment, the tail handle 10 should have a front end limit relative to the housing 17; otherwise it cannot meet the needs of puncture depth adjustment accuracy. In the present invention, in order to achieve that the tail handle 10 should have a front end limit relative to the housing 17, between the tail handle 10 and the housing 17, one is provided with an axial limit surface 4, and the other is provided with a limit action part 19. The axial limit surface 4 contacts fits with the limit action part 19 to limit the position where the tail handle 10 slides forward in the axial direction relative to the housing 17. In this embodiment, the axial limit surface 4 is located on the housing 17 (see FIG. 5-FIG. 7), and the limit action part 19 is located on the tail handle 10 (see FIG. 11-FIG. 13).

On the present invention, the rear puncture depth adjustment structure is composed of a ejection pin 6, a tail handle 10, and a return spring 29. The rear of the ejection pin 6 is equipped with an active impact surface 7 (see FIG. 4), which is facing towards the front of the lancing device. The active impact surface 7 is correspondingly equipped with a passive impact surface 13 on the sleeve structure of the tail handle 10 (see FIG. 8-FIG. 11), which is facing towards the rear of the lancing device. In this embodiment, the passive impact surface 13 is a spiral step surface on the sleeve structure of the tail handle 10, which is facing towards the rear of the lancing device (see FIG. 8-FIG. 10). This design belongs to the condition where the passive impact surface 13 is directly formed by a spiral action surface on the tail handle 10 in the present invention. Specifically, the tail handle 10 has a sleeve structure, which has an inner end face facing towards the rear of the lancing device. The spiral action surface is a spiral step surface, which is directly set on the inner end face of the tail handle 10 sleeve structure.

In order to install a return spring 29 between the ejection pin 6 and the tail handle 10, the rear of the ejection pin 6 is equipped with a rear end face 16 (see FIG. 4) for supporting the return spring 29, which faces towards the front of the lancing device. A front end face 18 (see FIG. 8 and FIG. 10) is arranged on the inner edge of the sleeve structure of the tail handle 10, which is used to support the return spring 29, corresponding to the rear end face 16. The front end face 18 faces towards the rear of the lancing device.

In order to provide a sense of gear shift for the tail handle 10 during the puncture depth adjustment process, the tail handle 10 is equipped with a rotating positioning structure in the circumferential direction of the lancing device relative to the housing 17. The rotating positioning structure is composed of a rotating positioning groove 11 and a rotating positioning block 12, one of which is located on the tail handle 10 and the other is located on the housing 17 or on a component fixedly connected to the housing 17. In this embodiment, the rotating positioning groove 11 is located on the outer edge of the tail of the middle sleeve 2 (see FIG. 3), while the rotating positioning block 12 is located on the inner edge of the inner sleeve 9 (see FIG. 10).

The two cooperate to form a rotating positioning structure. When the tail handle 10 is rotated, it intermittently rotates in a circumferential direction relative to the housing 17, while emitting clicking sounds. The middle sleeve 2 is a part of the shell, and it is fixedly connected to the housing 17. The length direction of the rotating positioning groove 11 is parallel to the axis of the lancing device, and each rotating positioning groove 11 is arranged at intervals in the circumferential direction of the lancing device.

On this embodiment, the sleeve structure of the main body of the tail handle 10 is composed of an outer sleeve 8 and an inner sleeve 9. In the assembly state, the inner sleeve 9 is fixed on the inner side of the front end of the outer sleeve 8, the guide protrusion 15 is arranged on the outer edge of the inner sleeve 9 or the outer sleeve 8, and the passive impact surface 13 is arranged on the end face of the inner sleeve 9 facing towards the rear of the lancing device (see FIG. 11-FIG. 13). In order to facilitate the assembly of the outer sleeve 8 and the inner sleeve 9, a positioning boss 24 is provided on the outer edge of the inner sleeve 9 (see FIG. 11), and a positioning groove 25 is provided on the inner edge of the outer sleeve 8 corresponding to the position of the positioning boss 24 (see FIG. 11). In the assembly state, the positioning boss 24 on the inner sleeve 9 fits with the positioning groove 25 on the outer sleeve 8 (see FIG. 12), to limit free degree of circumferential rotation of the inner sleeve 9 relative to the outer sleeve 8. At the same time, a positioning convex rib 26 (see FIG. 11) is provided on the outer edge of the inner sleeve 9, which is perpendicular or at an angle to the axis of the lancing device. Corresponding to the positioning convex rib 26, a positioning snap 28 (see FIG. 11) is arranged on the inner edge of the outer sleeve 8. In the assembly state, the positioning convex rib 26 on the inner sleeve 9 fits with the positioning snap 28 on the outer sleeve 8 (see FIG. 12), limiting free degree of axial movement of the inner sleeve 9 relative to the outer sleeve 8. This makes the outer sleeve 8 fixes and connects to the inner sleeve 9.

Figure 6:
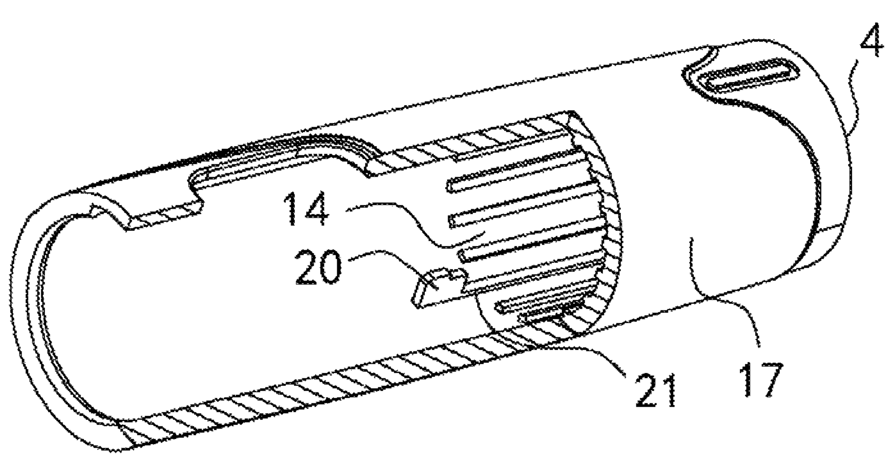
FIG. 6 is a partial three-dimensional cross-sectional view of the housing of Embodiment 1 of the lancing device of the present invention.
Figure 7:
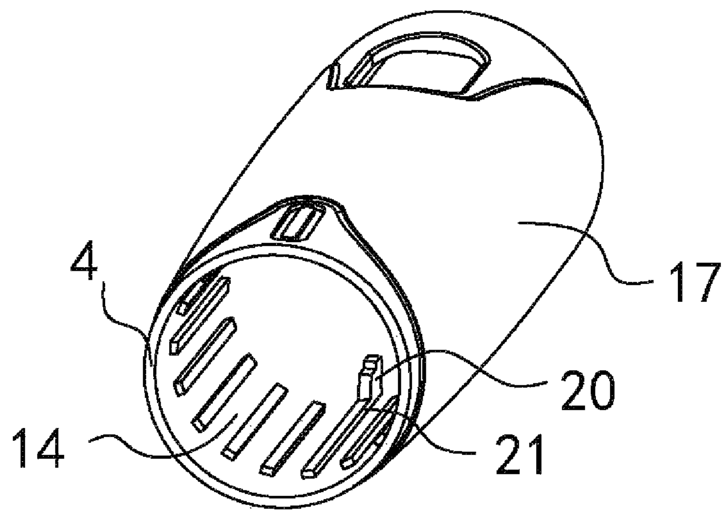
FIG. 7 is a three-dimensional view of the housing of Embodiment 1 of the lancing device of the present invention.
Figure 11:
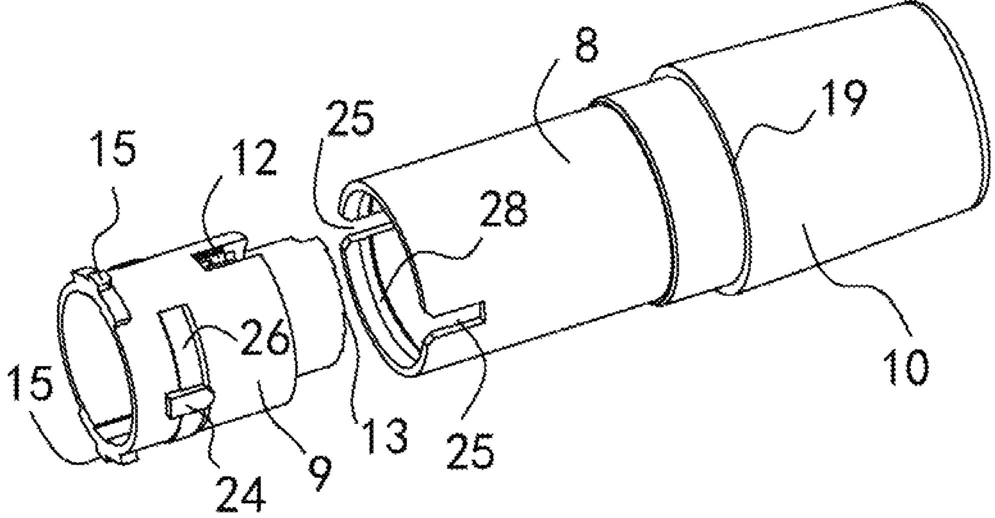
FIG. 11 is a three-dimensional exploded view of the tail handle of Embodiment 1 of the lancing device of the present invention.
Figure 12:
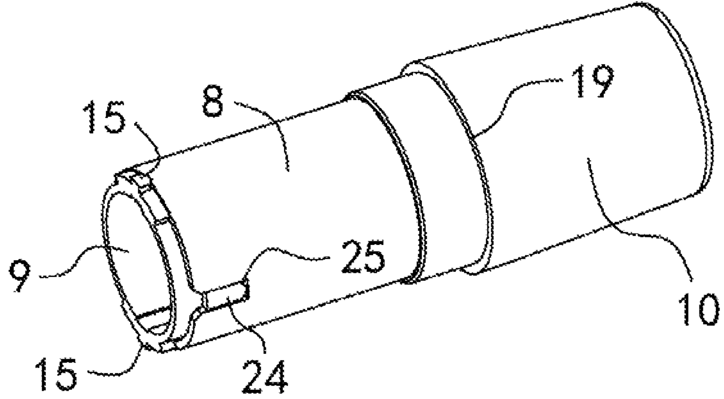
FIG. 12 is a three-dimensional view of the tail handle of Embodiment 1 of the lancing device of the present invention.
Figure 13:
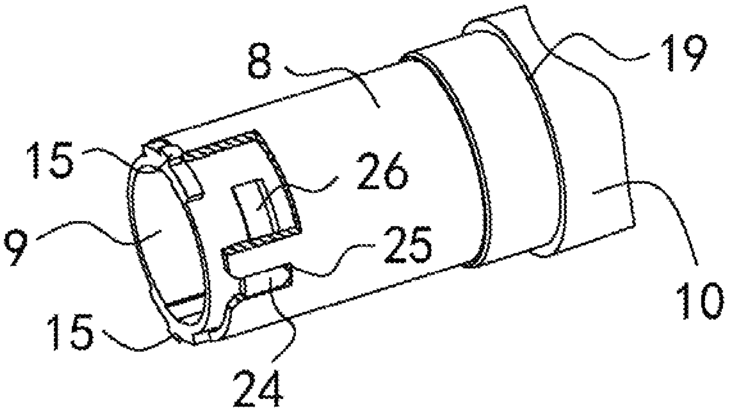
FIG. 13 is a three-dimensional view of the tail handle of Embodiment 1 of the lancing device of the present invention, accompanied by a partial cross-sectional view.
Figure 14:
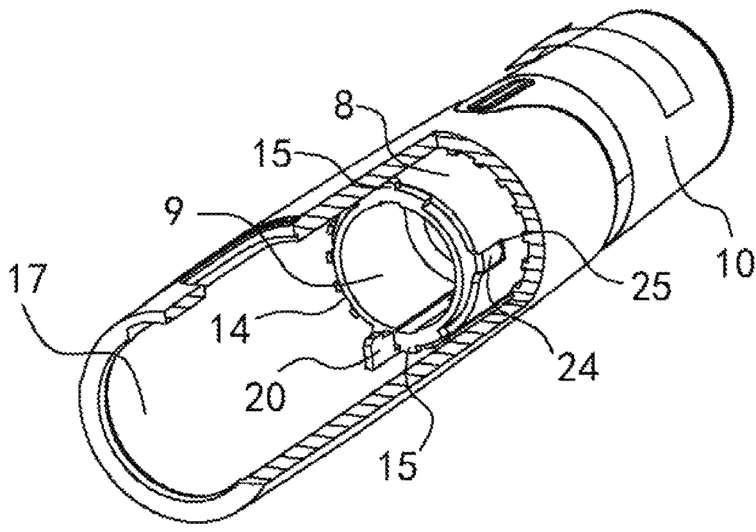
FIG. 14 a first perspective three-dimensional view of the assembly relationship between the tail handle and the housing of Embodiment 1 of the lancing device of the present invention.
Figure 15:
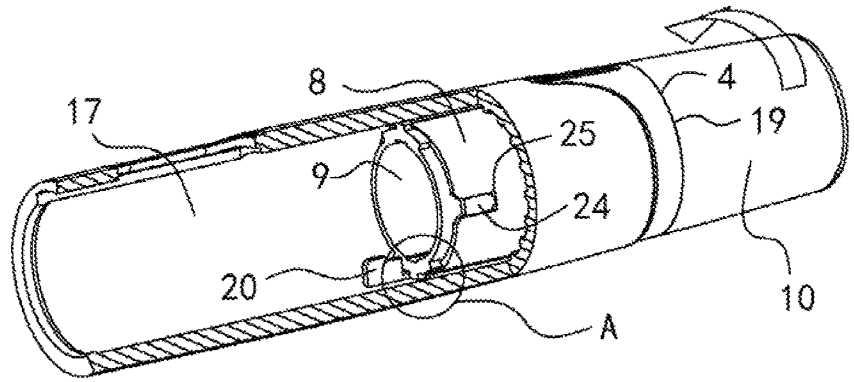
FIG. 15 a second perspective three-dimensional view of assembly relationship between the tail handle and the housing of Embodiment 1 of the lancing device of the present invention.
Figure 16:
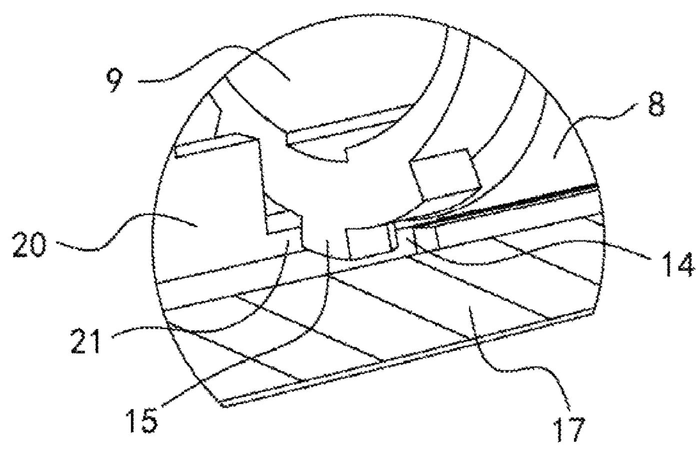
FIG. 16 is an enlarged view of A in FIG. 15.
Figure 17:
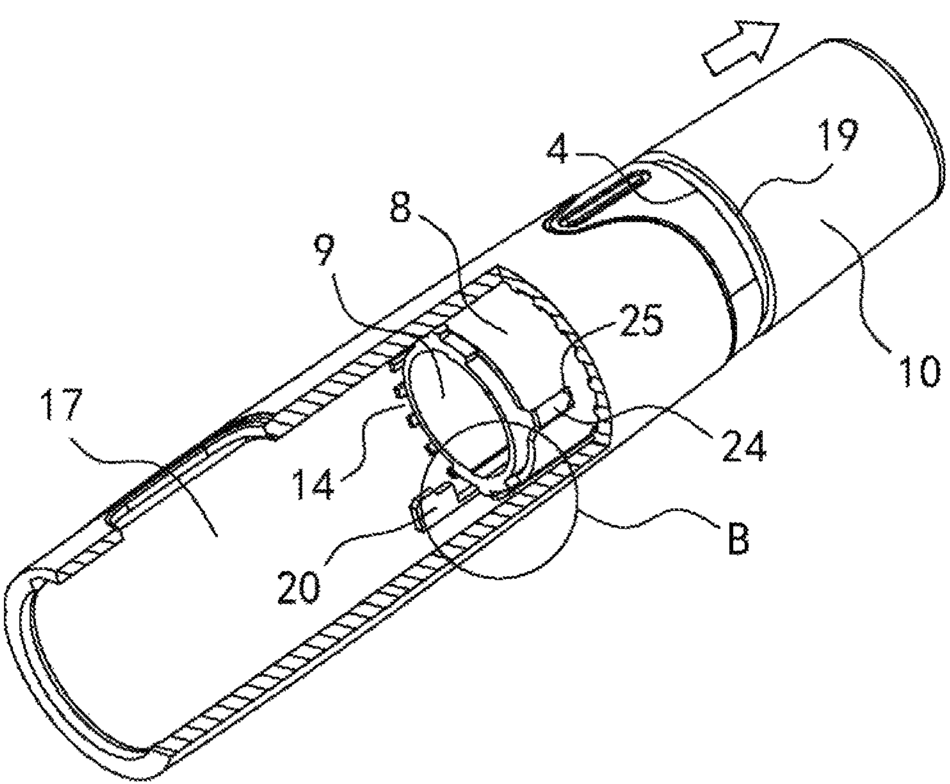
FIG. 17 is a three-dimensional view of movement relationship between the tail handle and the housing of Embodiment 1 of the lancing device of the present invention.
Figure 18:
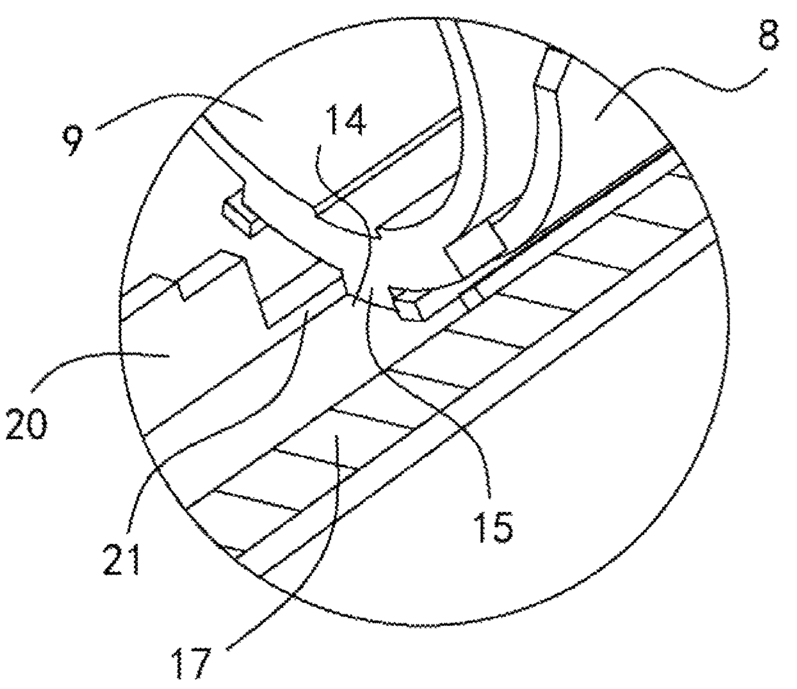
FIG. 18 is an enlarged view of B in FIG. 17.

In this embodiment, the inner edge of the housing 17 is equipped with a rotating limit convex rib 20 (see FIG. 5-7), and the rotating limit convex rib 20 is equipped with a corner limit surface 21 facing the circumferential direction of the lancing device (see FIG. 6). When the guide protrusion 15 and the guide slot 14 are in a non-cooperative working state, the combination of the guide protrusion 15 and the corner limit surface 21 can limit the circumferential rotation amplitude of the tail handle 10 relative to the shell (see FIG. 15 and FIG. 16).

Figures 19, 20:
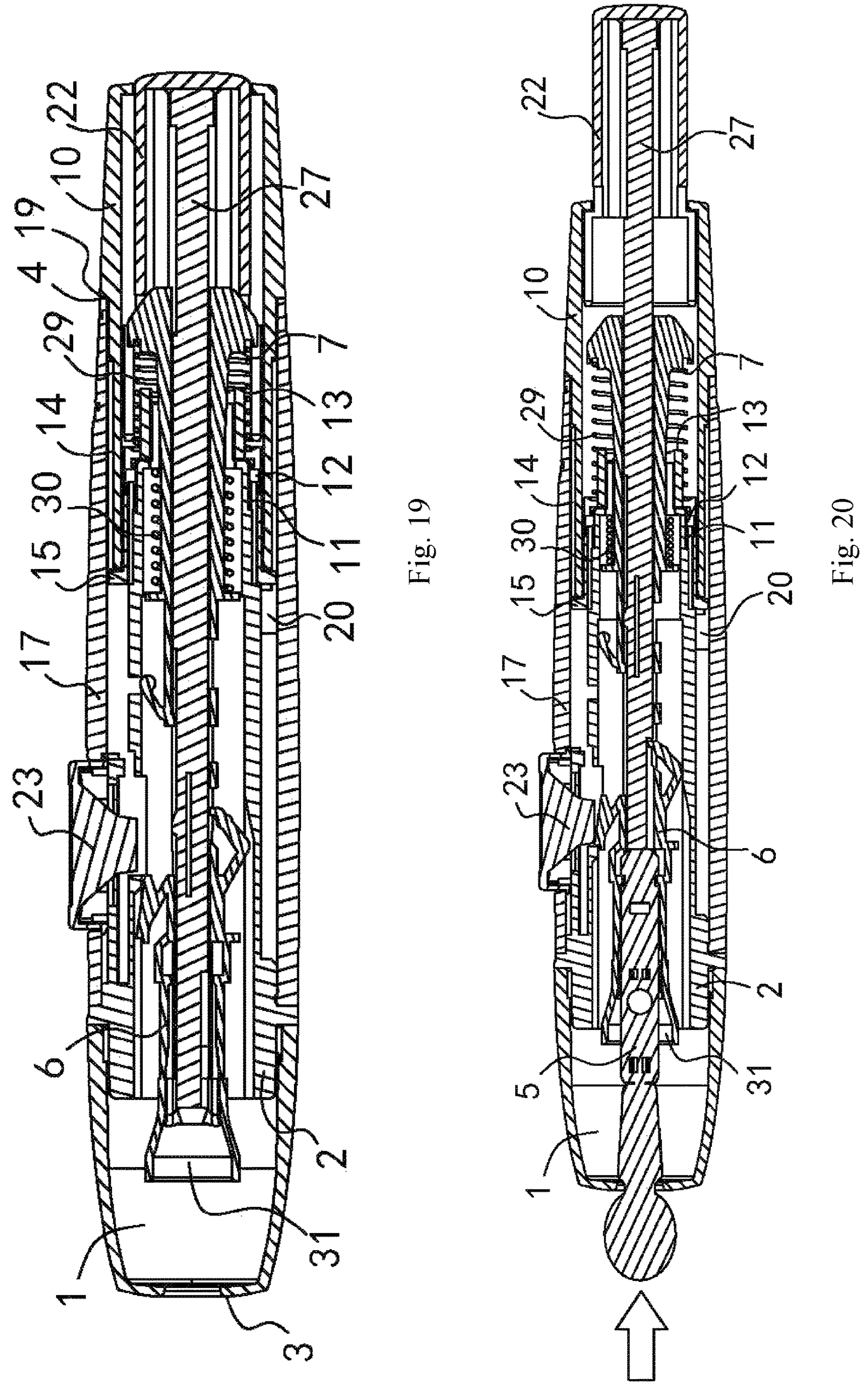
FIG. 19 is an initial assembly state diagram of Embodiment 1 of the lancing device of the present invention.
FIG. 20 is a state diagram of directly pressing lancet to load after the lancet being installed of Embodiment 1 of the lancing device of the present invention.

In this embodiment, the shell is composed of a cap 1, a housing 17, and a middle sleeve 2 (see FIG. 19). The main body of the middle sleeve 2 is a cylindrical structure, the middle sleeve 2 is located inside the housing 17 and fixedly connected to the housing 17, and the cap 1 is located at the front of the housing 17 and detachably fixedly connected to the housing 17 (see FIG. 19).

In order to better understand relative positions and relationships between various components in the present invention, the following describes the lancing device of the present invention in conjunction with its usage status:

1. Initial Assembly State

FIG. 19 shows the initial assembly state diagram of the embodiment of the lancing device of the present invention. The relative positions and relationships between various components in the initial assembly state can be seen from FIG. 19. In the initial assembly state, the front of the sleeve structure of the tail handle 10 is inserted into the rear of the housing 17, and the rear of the sleeve structure of the tail handle 10 is exposed to the back outer or middle outer side of the lancing device for facilitating manual operation by the user. The rear of the ejection pin 6 is inserted into the sleeve structure of the tail handle 10. One end of the launch spring 30 is positioned on the ejection pin 6, and the other end is positioned on the inner end face of the middle sleeve 2. The launch spring 30 acts on the ejection direction of the ejection pin 6. The return spring 29 is installed at the rear of the ejection pin 6, with one end of the return spring 29 resting against the front end face 18 of the tail handle 10 and the other end resting against the rear end face 16 of the ejection pin 6. Under the action of the return spring 29, the axial limit surface 4 between the tail handle 10 and the housing 17 contacts fit with the limit action part 19, causing the tail handle 10 to be in the front limit position relative to the shell, that is, the tail handle 10 is in an initial equilibrium position.

When the tail handle 10 is in the initial equilibrium position, the guide protrusion 15 and guide slot 14 between the tail handle 10 and the housing 17 are arranged in a staggered manner in the axial direction of the lancing device and are in a non-cooperative working state. When the guide protrusion 15 and the guide slot 14 are in a non-cooperative working state, manually rotating the exposed part of the rear of the tail handle 10 will drive the passive impact surface 13 on the sleeve structure of the tail handle 10 to rotate in a circumferential direction relative to the active impact surface 7 at the rear of the ejection pin 6. During the circumferential rotation process of the tail handle 10, due to the constraints of the rotation positioning structure, the tail handle 10 intermittently rotates in a circumferential direction relative to the shell and stays at different positioning positions in the circumferential direction. Due to the fact that the passive impact surface 13 is a spiral stepped surface, spiral surface, or inclined surface, the distance between the lancing end face 3 and the passive impact surface 13 in the axial direction of the lancing device is changed to adjust the lancet tip puncture depth.

2. Lancet Loading State

FIG. 20 shows a state diagram of directly pressing lancet to load after the lancet being installed of embodiment of the lancing device of the present invention.

Due to the fact that the lancet hole at the front end of cap 1 has been designed as a large hole, the lancet 5 is directly inserted into the lancet holder 31 through this large hole. Therefore, when installing the lancet, it is not necessary to remove cap 1. Instead, the lancet 5 can be directly inserted from the blood collection port of cap 1. At this time, the tail end face of the lancet 5 is rested against the front end face of the lancet unloading rod 27. Continue inserting the lancet 5, pushing the lancet unloading rod 27 and unloading push handle 22 back until the ejection pin 6 is loaded and locked; the lancet 5 will be clamped by the lancet holder 31.

After the completing loading of the ejection pin 6 of lancing device, as the tail handle 10 is still in the initial equilibrium position, if adjusting the puncture depth of the lancing device is needed in this state, rotating and operating the tail handle 10 will achieve this.

3. Protective Cap Removing State

Figures 21, 22:
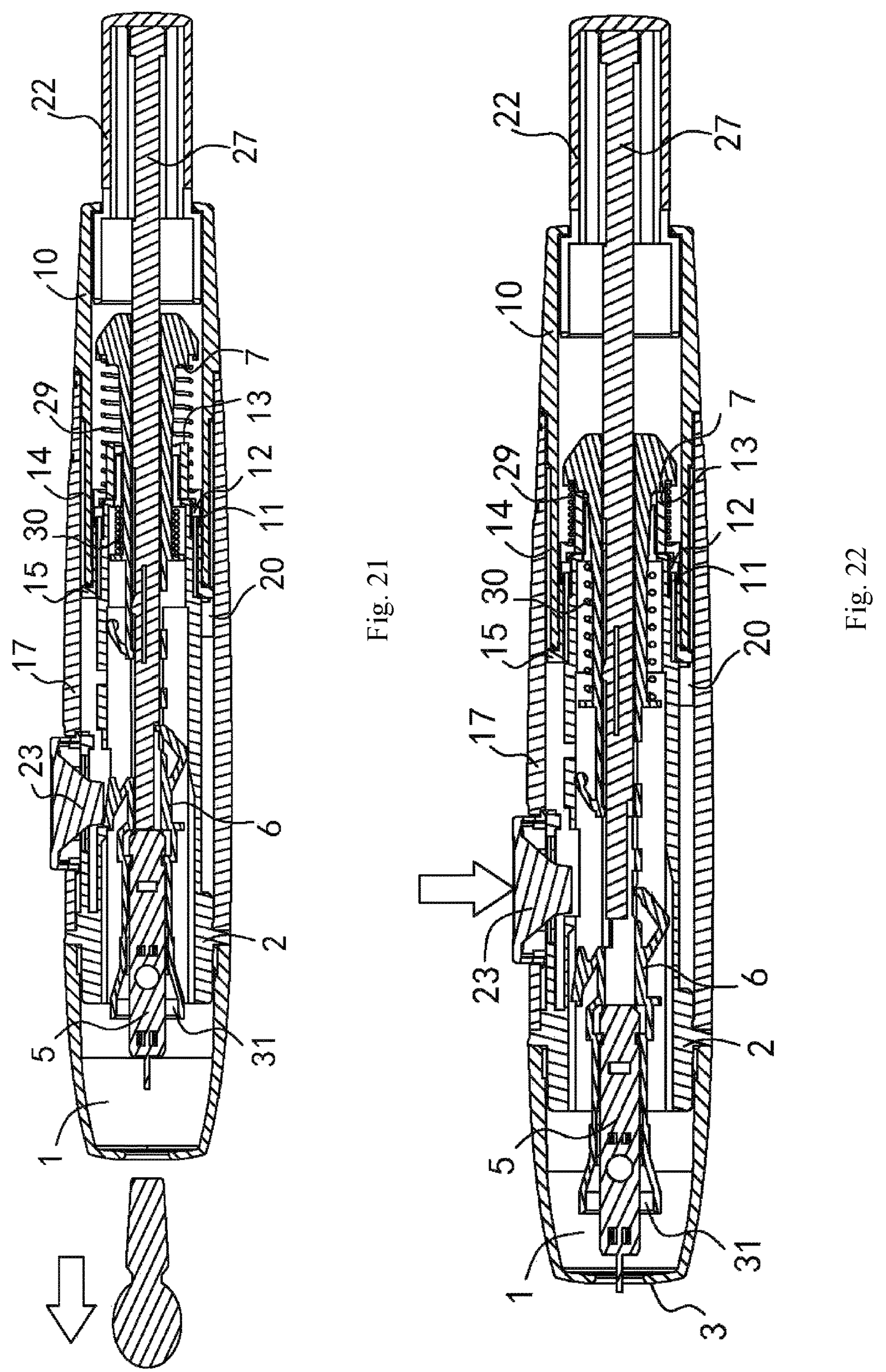
FIG. 21 is a state diagram of removing the protective cap of the lancet of Embodiment 1 of the lancing device of the present invention.
FIG. 22 is a state diagram of collecting blood by pressing button to eject of Embodiment 1 of the lancing device of the present invention.

FIG. 21 shows the state diagram of removing the protective cap of the lancet in the embodiment of the present invention. From FIG. 21, it can be seen that the protective cap on the lancet 5 is twisted off.

After twisting off the protective cap on lancet 5, as the tail handle 10 is still in the initial equilibrium position, adjusting the puncture depth of the lancing device is needed in this state, rotating and operating the tail handle 10 will achieve this.

4. Ejecting and Lancing State

FIG. 22 is a state diagram of collecting blood by pressing button to eject of the embodiment of the lancing device of the present invention. In this state, pressing button 23 to force the ejection pin 6 to unhook, the launch spring 30 pushes the ejection pin 6 and the lancet 5 to move forward. During the forward movement and ejection process, the ejection pin 6 and the lancet 5 first compress the return spring 29, and then the active impact surface 7 (see FIG. 4) at the rear of the ejection pin 6 collides with the passive impact surface 13 (see FIG. 8-FIG. 11) on the sleeve structure of the tail handle 10 to stop the ejection pin 6 from moving forward, while the lancet 5 ejected and punctured skin.

5. Restoring Natural State

Figures 23, 24:
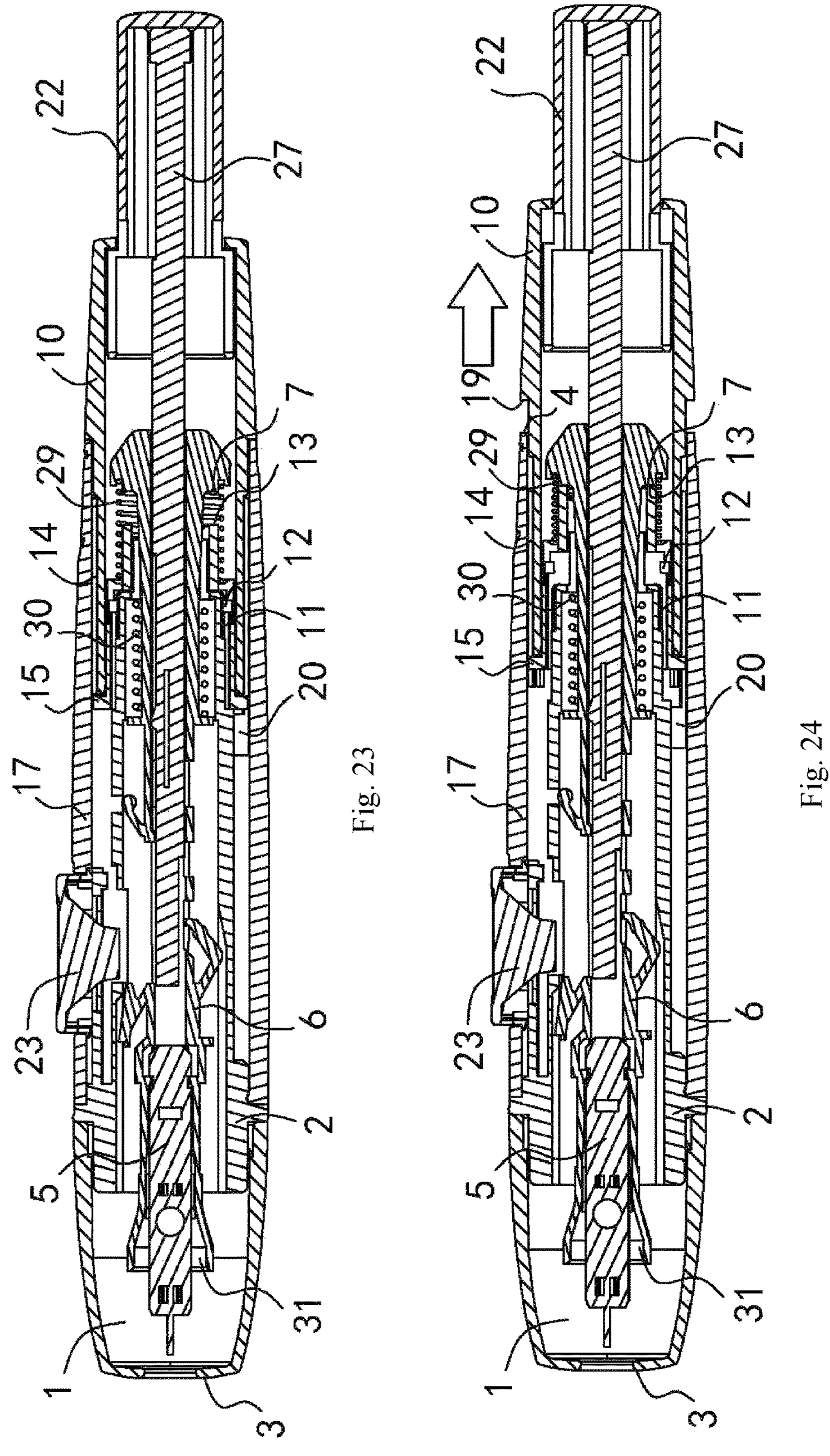
FIG. 23 is a state diagram of restoring natural after ejecting to collecting blood of Embodiment 1 of the lancing device of the present invention.
FIG. 24 is an initial state diagram of using the tail handle to load of Embodiment 1 of the lancing device of the present invention.

FIG. 23 is a state diagram of restoring natural after ejecting to collecting blood of the embodiment of the lancing device of the present invention. From FIG. 23, it can be seen that under the influence of the return spring 29, the ejector pin 6 returns to its initial position.

After blood collection, if it is found that due to insufficient puncture depth, insufficient blood collection volume, or no blood collection, and the tail handle 10 is still in the initial equilibrium position, if adjusting the puncture depth of the lancing device is needed in this state, rotating and operating the tail handle 10 will achieve this.

6. Initial State of Utilizing the Tail Handle to Load

FIG. 24 is an initial state diagram of using the tail handle to load of the embodiment of the lancing device of the present invention. In this state, manually pulling back on the exposed part of the rear of the tail handle 10, the sleeve structure of the tail handle 10 overcomes the elasticity of the return spring 29 and moves axially relative to the housing 17. At this time, the tail handle 10 leaving the initial equilibrium position, the guide protrusion 15 and guide slot 14 between the tail handle 10 and the housing 17 changes from being arranged in a staggered manner (in a non-cooperative working state) in the axial direction of the lancing device to being arranged in overlapping manner in the axial direction of the lancing device, and in cooperative working state, the tail handle 10 cannot rotate relative to the housing 17. In other words, during the axial movement of the tail handle 10 towards the rear, the guide slot 14 between the outer edge of the tail handle 10 and the inner edge of the housing 17 slides fit with the guide protrusion 15, and plays a guiding role in the axial direction of the lancing device. Due to the sliding fit constraint of the guide slot 14 and the guide protrusion 15, in this state, the freedom of the tail handle 10 to rotate in a circumferential direction relative to the shell is lost, and it cannot rotate but only slide axially.

7. Loading State of Tail Handle

Figures 25, 26:
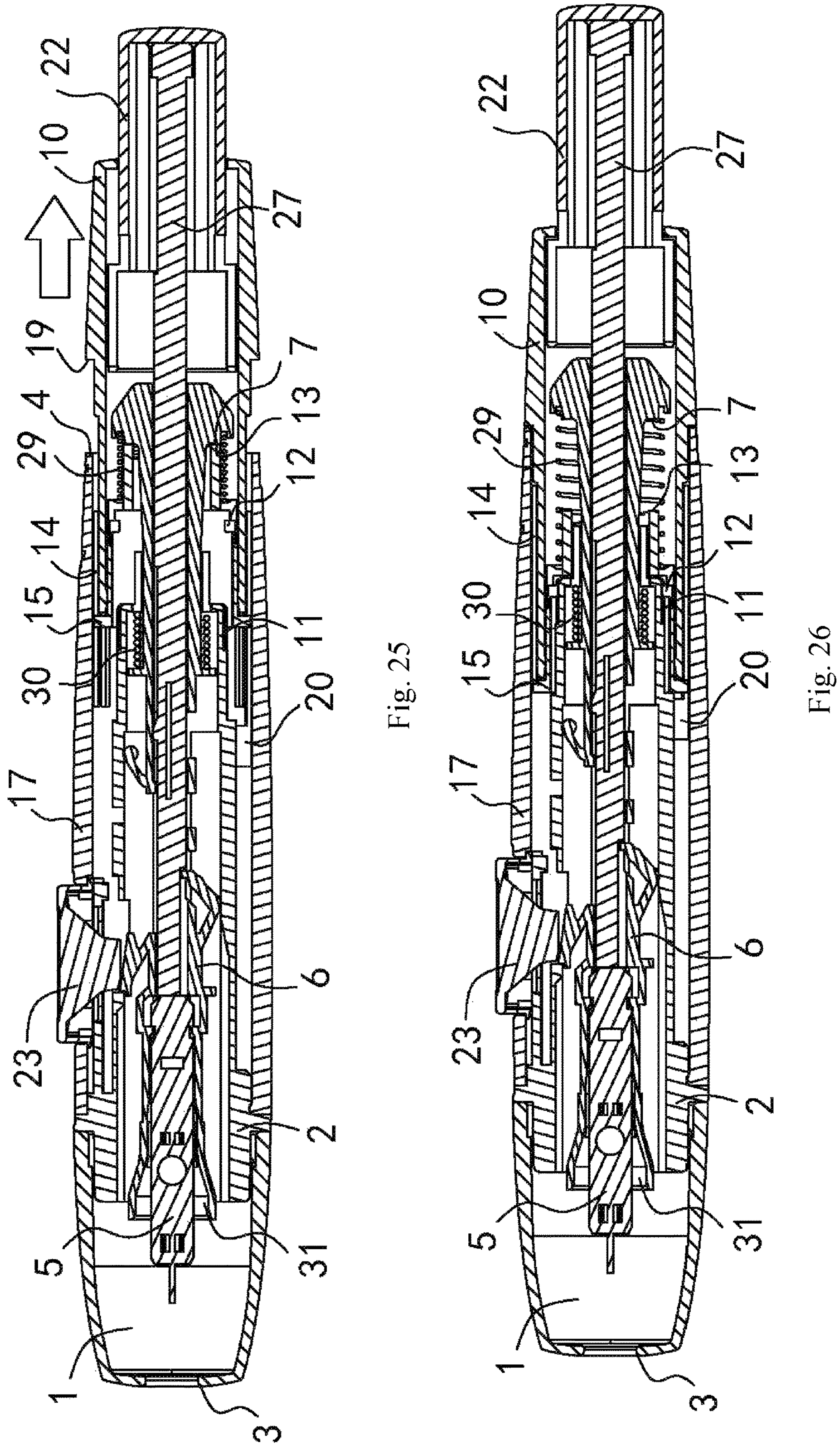
FIG. 25 is a state diagram of using the tail handle to load of Embodiment 1 of the lancing device of the present invention.
FIG. 26 is a completion state diagram of using the tail handle to load of Embodiment 1 of the lancing device of the present invention.

FIG. 25 shows a state diagram of using the tail handle to load of the embodiment of the lancing device of the present invention. On the basis of the previous state, continuing to pull the tail handle 10, after overcoming the elastic force of the launch spring 30, force the passive impact surface 13 to contact the active impact surface 7 at the rear of the ejection pin 6, and drive the ejection pin 6 to move backward relative to the housing 17 until the ejection pin 6 is loaded and locked.

8. Completing Loading State of Tail Handle

FIG. 26 shows a completion state diagram of using the tail handle to load of the embodiment of the lancing device of the present invention. After manually pulling the tail handle 10 backward to make the ejection pin 6 loaded and locked, release the tail handle 10 under the elastic force of the return spring 29, the tail handle 10 moves axially forward relative to the housing 17 until it stops at the initial equilibrium position again. At this point, the guide protrusion 15 and guide slot 14 between the tail handle 10 and the housing 17 change from overlapping arrangement in the axial direction of the lancing device, returning to a state of staggered arrangement in the axial direction of the lancing device.

In this state, as the tail handle 10 is still in the initial equilibrium position, if adjusting the puncture depth of the lancing device is needed, rotating and operating the tail handle 10 will achieve this.

From this, it can be seen that starting from the initial equilibrium position of the tail handle 10, manually pulling the tail handle 10 backward can enable the guide protrusion 15 and guide slot 14 between the tail handle 10 and the housing 17 to switch between non-cooperative working state and cooperative working state.

9. Initial State of Unloading Lancet

Figures 27, 28:
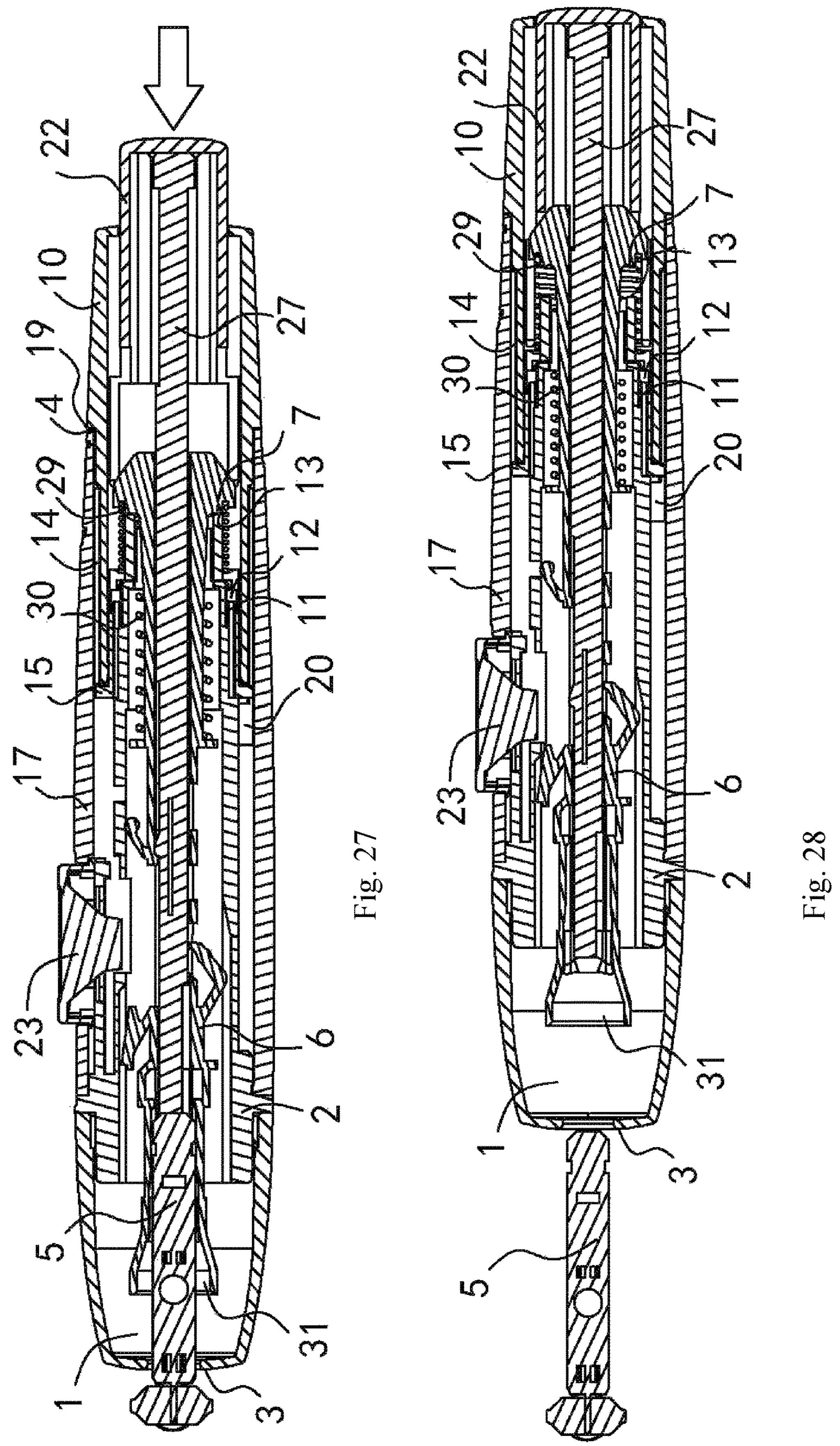
FIG. 27 is an initial state diagram of pressing the unloading push handle to unload lancet of Embodiment 1 of the lancing device of the present invention.
FIG. 28 is a secondary restoring initial state diagram after unloading the lancet of Embodiment 1 of the lancing device of the present invention.

FIG. 27 is an initial state diagram of pressing the unloading push handle to unload lancet of the embodiment of the lancing device of the present invention. Pressing the unloading push handle 22, the front end face of the lancet unloading rod 27 will rest against the rear end face of the lancet 5 and move forward. As the lancet 5 is clamped by the lancet holder 31, the ejection pin 6 is driven forward, until the active impact surface 7 at the rear of the ejection pin 6 contacts the passive impact surface 13 on the tail handle 10, and the ejection pin 6 stops moving forward. Continuing to press the unloading push handle 22, as the ejection pin 6 is relatively fixed, the lancet 5 is pushed out of the lancet holder 31 by the lancet unloading rod 27.

10. Restoring Initial State

FIG. 28 is a secondary restoring initial state diagram after unloading the lancet of Embodiment 1 of the lancing device of the present invention. Continuing to press the unloading push handle 22 on the basis of the previous state until the lancet 5 is completely pushed out by the unloading push handle 27, the lancet 5 automatically falls off from the cap 1 under the influence of gravity, and at this time, the ejection pin 6 returns to its initial position.

Embodiment 2: A Lancing Device Utilizing Tail Handle to Load and Adjust Depth

The difference between Embodiment 2 and Embodiment 1 is that the puncture depth adjustment mechanism is different. Specifically, the passive impact surface 13 in the puncture depth adjustment mechanism has a different form reflected by the spiral action surface on the tail handle 10. In Embodiment 1, the passive impact surface 13 is directly formed by the spiral action surface on the tail handle 10. In Embodiment 2, the passive impact surface 13 is indirectly formed by the spiral action surface on the tail handle 10. In Embodiment 2, the passive impact surface 13 is indirectly formed by the spiral action surface on the tail handle 10. Whether in Embodiment 1 or Embodiment 2, rotating the tail handle 10 can both change the position of impact point on the passive impact surface 13 in the axial direction of the lancing device, thereby changing the distance between the lancing end face 3 and the impact point on the passive impact surface 13 in the axial direction of the lancing device, for adjusting the lancet tip puncture depth.

Figure 29:
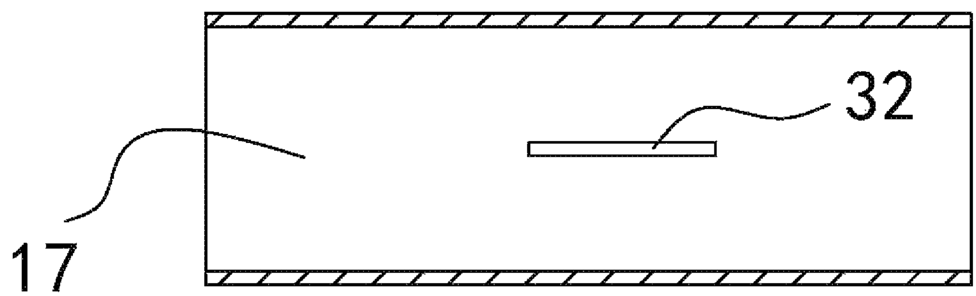
FIG. 29 is a cross-sectional view of the housing of Embodiment 2 of the lancing device of the present invention.
Figure 32:
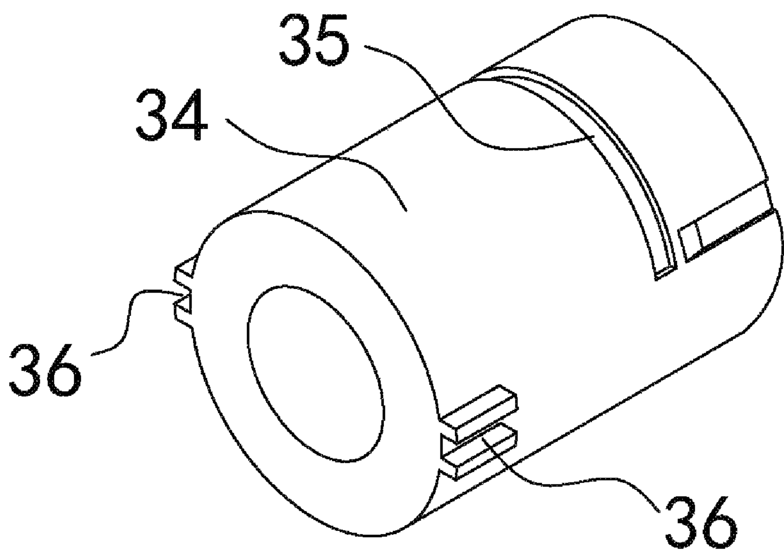
FIG. 32 is a three-dimensional view of the sliding sleeve of Embodiment 2 of the lancing device of the present invention.
Figure 33:
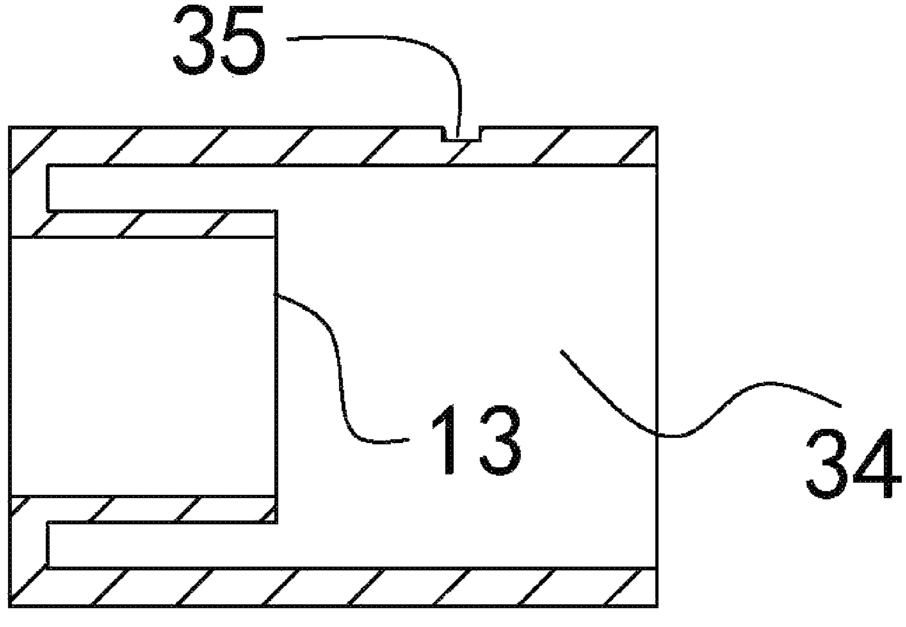
FIG. 33 is a cross-sectional view of the sliding sleeve of Embodiment 2 of the lancing device of the present invention.
Figure 34:
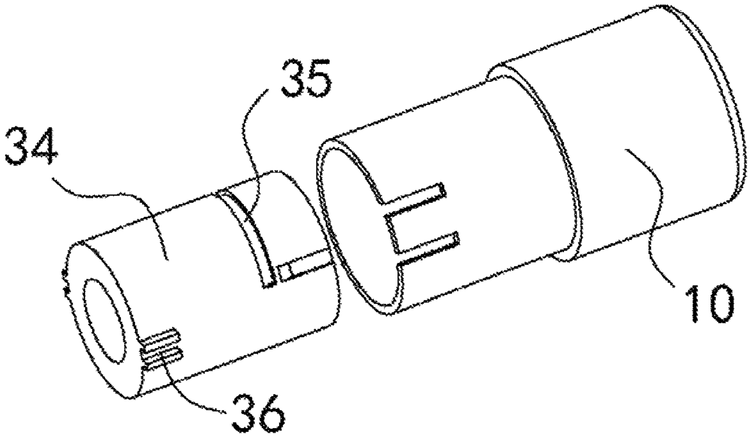
FIG. 34 is a three-dimensional exploded view of the tail handle and sliding sleeve of Embodiment 2 of the lancing device of the present invention.
Figure 35:
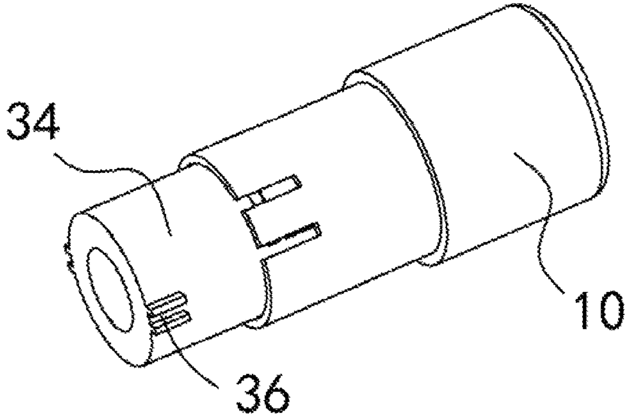
FIG. 35 is a three-dimensional assembly view of the tail handle and sliding sleeve of Embodiment 2 of the lancing device of the present invention.
Figure 36:
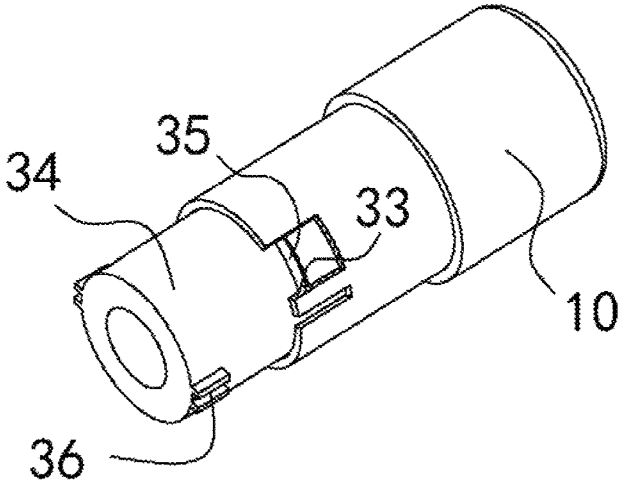
FIG. 36 is a three-dimensional assembly view of the tail handle and sliding sleeve of Embodiment 2 of the lancing device of the present invention (with partial section)

In Embodiment 2, the passive impact surface 13 is indirectly formed by a spiral action surface on the tail handle 10. Specifically, a sliding sleeve 34 is provided for the tail handle 10 (see FIGS. 32 and 33), and the sliding sleeve 34 is positioned and connected in the circumferential direction of the lancing device relative to the housing 17, while sliding and connected in the axial direction of the lancing device. In Embodiment 2, the specific implementation method is as follows: in the assembly state, the sliding sleeve 34 is located inside the housing 17, with a guide rib 32 (see FIG. 29) on the inner wall of the housing 17, and a guide groove 36 (see FIG. 32) on the outer wall of the sliding sleeve 34. The guide rib 32 cooperates with the guide groove 36 to enable the sliding sleeve 34 to slide along the axial direction of the lancing device relative to the housing 17, and cannot rotate around the axis.

Figure 30:
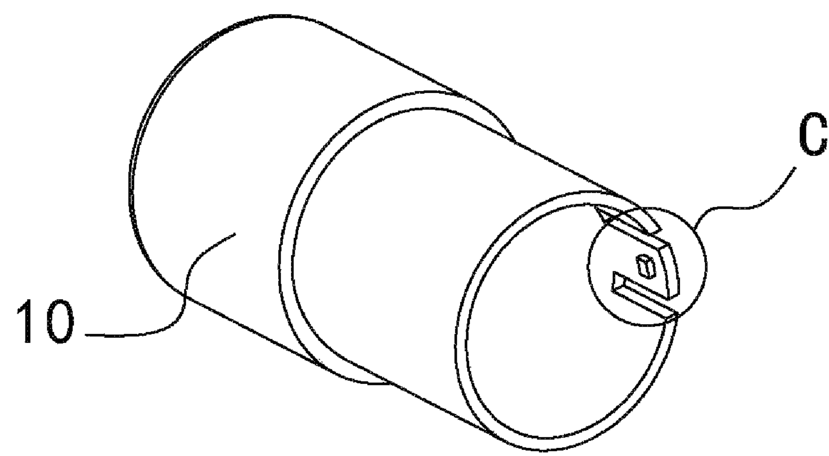
FIG. 30 is a three-dimensional view of the tail handle of Embodiment 2 of the lancing device of the present invention.
Figure 31:
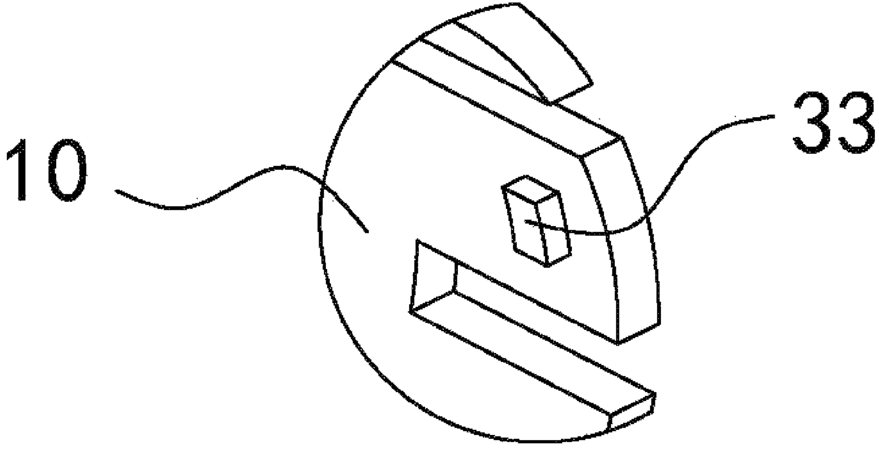
FIG. 31 is an enlarged view of C in FIG. 30.

The tail handle 10 is connected to the sliding sleeve 34 through a screw pair, forming an axial movement mechanism of the sliding sleeve 34 that is adjusted by the rotation of the tail handle 10. The passive impact surface 13 is an inner end face of the sliding sleeve 34 (see FIG. 33), and the spiral action surface is a screw pair. The screw pair is formed by the combination of the spiral groove 35 and the driving block 33. One of the spiral groove 35 and the driving block 33 is located on the tail handle 10, and the other is located on the sliding sleeve 34. In Embodiment 2, the spiral groove 35 is located on the sliding sleeve 34 (see FIG. 32), while the driving block 33 is located on the tail handle 10 (see FIGS. 30 and 31). Of course, the setting positions of the spiral groove 35 and the driving block 33 can be exchanged.

Figure 37:
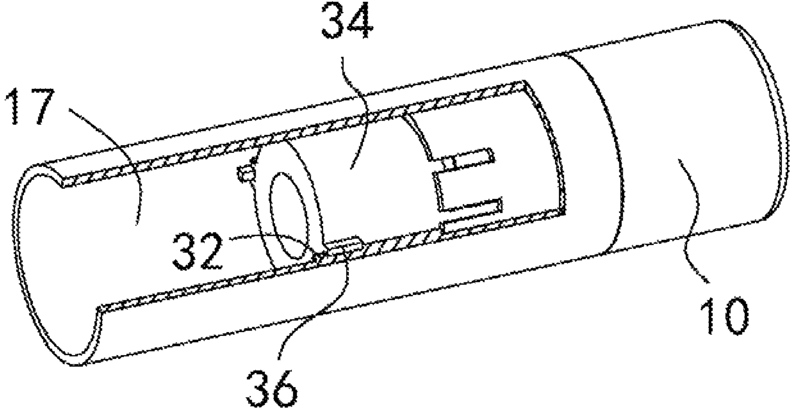
FIG. 37 is an initial state three-dimensional view of the assembly of the tail handle, sliding sleeve, and housing of Embodiment 2 of the lancing device of the present invention.
Figure 40:
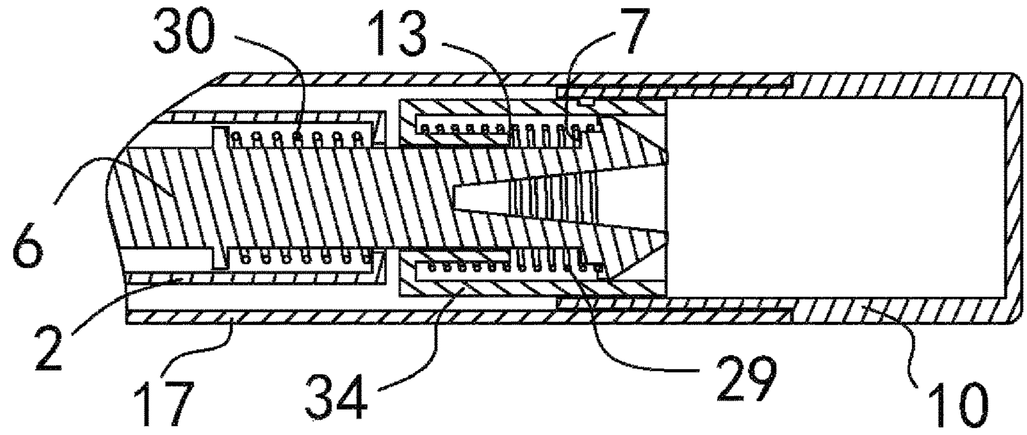
FIG. 40 is an initial state cross-sectional diagram of the tail handle of Embodiment 2 of the lancing device of the present invention.

FIG. 37 and FIG. 40 are initial states of the assembly of the tail handle 10, sliding sleeve 34, and housing 17 of Embodiment 2 of the lancing device of the present invention.

From the figures, it can be seen that in the initial state, the front end of the tail handle 10 extends into the inner rear of the housing 17, and the sliding sleeve 34 is also located inside the housing 17. Among them, the tail handle 10 and the housing 17 rotate in the circumferential direction of the lancing device and slide fit in the axial direction. The guide groove 36 on the outer edge of the sliding sleeve 34 matches with the guide rib 32 on the inner edge of the housing 17, and the spiral groove 35 on the outer edge of the sliding sleeve 34 and the driving block 33 on the inner edge of the tail handle 10.

Figure 38:
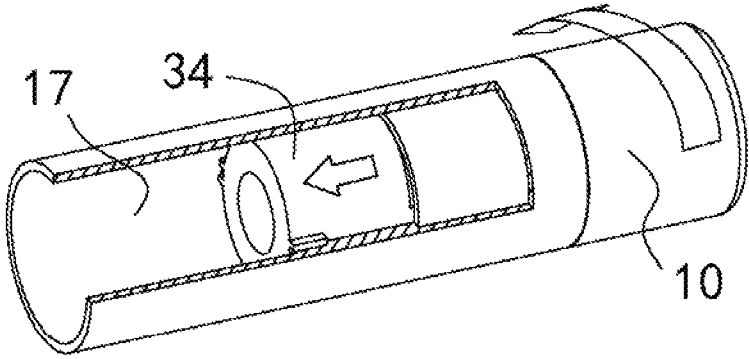
FIG. 38 is a three-dimensional view of the rotating state of the tail handle after the assembly of the tail handle, sliding sleeve, and housing of Embodiment 2 of the lancing device of the present invention.

FIG. 38 is a view of the rotating state of the tail handle after the assembly of the tail handle 10, sliding sleeve 34, and housing 17 of Embodiment 2. From the figure, it can be seen that when the tail handle 10 is turned (as shown by the arrow in FIG. 38), the sliding sleeve 34 is driven to slide axially to the left inside the housing 17 by the combination of the driving block 33 and the spiral groove 35 (as shown by the arrow in FIG. 38).

Due to the passive impact surface 13 (see FIG. 33) inside the sliding sleeve 34 moving to the left with sliding sleeve 34, the distance between the lancing end face 3 and the impact point on the passive impact surface 13 in the axial direction of the lancing device is changed to adjust the lancet tip puncture depth.

Figure 39:
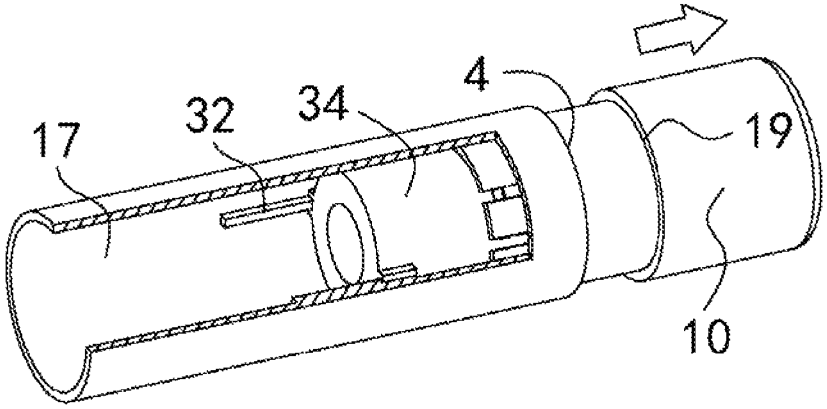
FIG. 39 is a three-dimensional view of the pulling state of the tail handle after the assembly of the tail handle, sliding sleeve, and housing of Embodiment 2 of the lancing device of the present invention.
Figure 41:
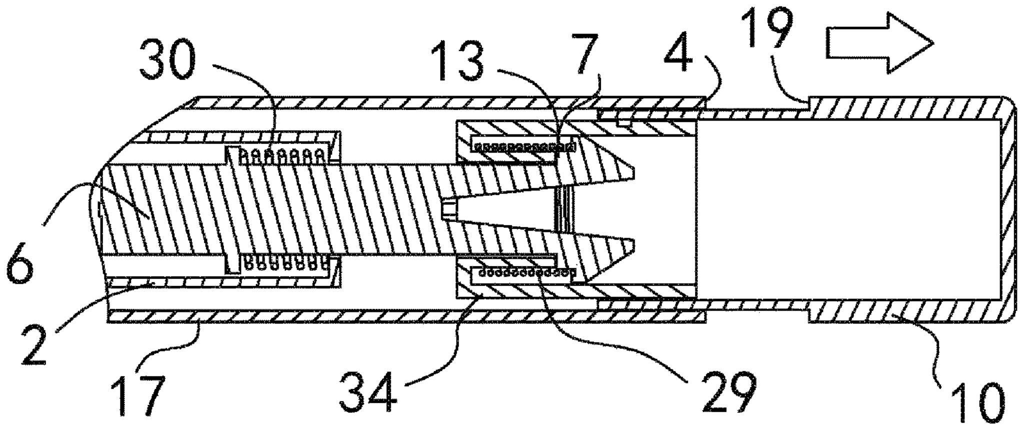
FIG. 41 is a loading state cross-sectional view of utilizing the tail handle at the rear of Embodiment 2 of the lancing device of the present invention.

FIG. 39 and FIG. 40 are views of pulling backward state of the tail handle after the assembly of the tail handle 10, sliding sleeve 34, and housing 17 of Embodiment 2. From the figures, it can be seen that when the tail handle 10 is pulled backward, it overcomes the force of the return spring 29 and forces the passive impact surface 13 to contact the active impact surface 7 at the rear of the ejection pin 6 (see FIG. 41), driving the ejection pin 6 to move backward relative to the shell until the ejection pin 6 is loaded and locked.

Figure 42:
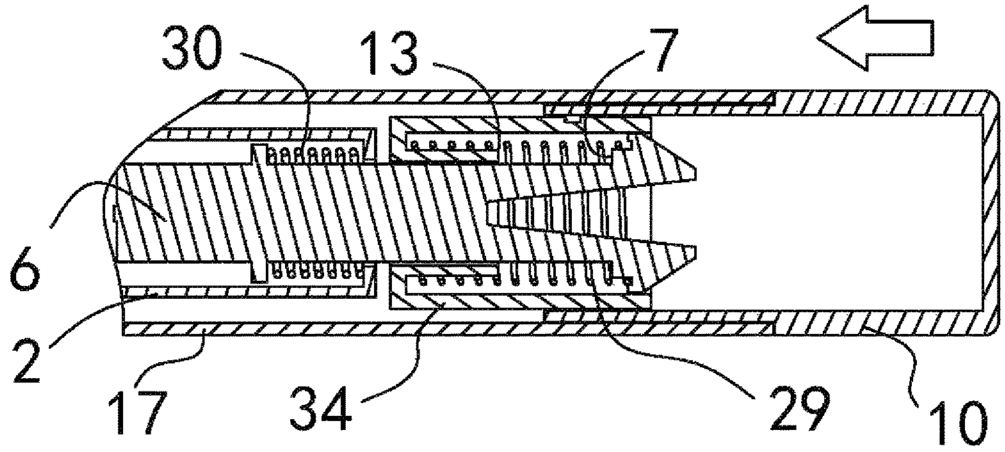
FIG. 42 is a cross-sectional view of the tail handle of Embodiment 2 of the lancing device of the present invention, which is automatically reset by using a return spring.

FIG. 42 is a diagram of the automatic reset state of the tail handle 10 using the return spring 29 in Embodiment 2. From the figure, it can be seen that after pushing backward the tail handle 10 to load, releasing the tail handle 10 under the elastic force of the return spring 29, the tail handle 10 moves axially forward relative to the housing 17, and the tail handle 10 will stop when it returns to the front limit position again.

In Embodiment 2, except for the above content, the other content is the same as the corresponding content in Embodiment 1, so the description will not be repeated here.

For the above embodiments, the possible changes that may occur in the present invention are described as follows:

1. In Embodiment 1 above, in order to ensure that the puncture depth of the tail handle 10 will not be changed during the backward pulling process, a composite fit section formed by the combination of the guide slot 14 and the guide protrusion 15 needs to be designed between the outer edge of the tail handle 10 and the inner edge of the housing 17. However, the present invention is not limited to this, in other words, such a composite fit section is not necessary for the present invention, but the best design. In the implementation of the present invention, canceling the design of the composite fit section can also achieve the purpose of the present invention, which is understandable and acceptable by those skilled in the art.

2. In Embodiment 1 above, the guide slot 14 is located on the inner edge of the housing 17 (see FIGS. 5-7), while the guide protrusion 15 is located on the outer edge of the tail handle 10 (see FIGS. 12 and 13). But the present invention is not limited to this, and the guide slot 14 may also be located on the outer edge of the tail handle 10, and the guide protrusion 15 may be located on the inner edge of the housing 17. This is understandable and acceptable by those skilled in the art. In addition, the guide protrusion 15 may be changed into a guide strip or a guide protrusion structure.

3. In Embodiment 1 above, in this embodiment, the axial limit surface 4 is located on the housing 17 (see FIG. 5-FIG. 7), and the limit action part 19 is located on the tail handle 10 (see FIG. 12-FIG. 13). However, the present invention is not limited to this, as both may be arranged on the tail handle 10 and the housing 17 in other parts. For example, using the rear end face facing the rear of the lancing device on the rotating limit convex rib 20 of the housing 17 to cooperate with the front end face facing the front of the lancing device on the inner sleeve 9 of the tail handle 10 may also replace the axial limit surface 4 and the limit action part 19, and have the effect of front end limit on the tail handle 10.

4. In Embodiment 1 above, the passive impact surface 13 is a spiral step surface facing behind the lancing device on the sleeve structure of the tail handle 10 (see FIG. 8-FIG. 10). However, the present invention is not limited to this, and the passive impact surface 13 may also be a spiral surface or an inclined surface. This is understandable and acceptable by those skilled in the art.

5. In Embodiment 1 above, the rotating positioning groove 11 is located on the outer edge of the tail of the middle sleeve 11 (see FIG. 3), while the rotating positioning block 12 is located on the inner edge of the inner sleeve 9 (see FIG. 10), and the two cooperate to form a rotating positioning structure. However, the present invention is not limited to this. On the one hand, the rotating positioning groove 11 and the rotating positioning block 12 can exchange positions, that is, the rotating positioning block 12 is located on the outer edge of the tail of the middle sleeve 11, while the rotating positioning groove 11 is located on the inner edge of the inner sleeve 9. On the other hand, the rotating positioning groove 11 and the rotating positioning block 12 may also be installed in other parts of the tail handle 10 and the housing 17. For example, the rotating positioning groove 11 is located on the outer edge of the outer sleeve 8, while the rotating positioning block 12 is located on the inner edge of the housing 17.

6. In Embodiment 1 above, the cap 1 is located at the front of the housing 17 and is detachably and fixedly connected to the housing 17 (see FIG. 19). However, the present invention is not limited to this. The pen cap 1 and the housing 17 may be designed as an integrated forming structure. The needle hole at the front end of the cap 1 is designed as a large hole, allowing the lancet 5 to be directly inserted into the lancet holder 31 through the large hole at the front end. When unloading the lancet, the lancet 5 can be directly removed from the large hole at the front end. This design can eliminate the action of removing the cap 1 during lancet installation, simplifying the operation. Another situation is that the cap 1 is located at the front of the housing 17 and can be detachably and fixedly connected to the housing 17. However, the needle hole at the front end of the cap 1 is designed with a small hole. When installing the lancet, the cap 1 needs to be removed first, and then the lancet 5 will be inserted into the lancet holder 31.

7. In Embodiment 1, when the tail handle 10 is in the initial equilibrium position, the guide protrusion 15 and guide slot 14 between the tail handle 10 and the housing 17 are arranged in a staggered manner along the axial direction of the lancing device and are in a non-cooperative working state. In this working state, the puncture depth during blood collection can be adjusted by rotating the tail handle 10. However, the present invention is not limited to this. The position that allows for adjusting the puncture depth is not necessarily arranged at the initial equilibrium position of the tail handle 10, and the position that allows for adjusting the puncture depth may also be arranged at the position after pulling the tail handle 10 axially for a certain distance, Firstly, pull the tail handle 10 backward for a certain distance before entering the position where the puncture depth can be adjusted (at this time, the guide protrusion 15 and guide slot 14 are arranged in a staggered position along the axial direction of the lancing device). Of course, it is more reasonable to arrange the tail handle 10 at the initial equilibrium position, allowing for adjustment of the puncture depth. As long as the tail handle 10 is at the initial equilibrium position, the puncture depth can be adjusted at any time regardless of whether the lancet is installed or whether being loaded.

8. In Embodiment 1 above, the lancet unloading rod 27 and the unloading push handle 22 form a tail lancet unloading structure in the lancing device. The present invention is not limited to this and can adopt a side lancet unloading structure. For lancing device, tail unloading and side unloading are two common lancet unloading structures in existing technology.

9. In Embodiment 1 above, the active impact surface 7 is located on the rear side of the ejection pin 6. The present invention is not limited to this, and the active impact surface 7 may be designed on the lancet 5.

10. In Embodiment 2 above, the screw pair is formed by matching the spiral groove 35 with the driving block 33. However, the present invention is not limited to this. The screw pair may also be formed by the combination of external and internal threads. One of the external and internal threads is located on the tail handle 10, and the other is located on the sliding sleeve. This is understandable and acceptable by those skilled in the art.

The above embodiments are only intended to illustrate the technical concept and characteristics of the present invention, and their purpose is to enable those familiar with the technology to understand the content of the present invention and implement it accordingly, without limiting the scope of protection of the present invention. Any equivalent changes or modifications made according to the essence of the present invention shall be covered within the scope of protection of the present invention.

The invention claimed is:

1. A lancing device utilizing a tail handle to load and adjust depth, comprising a shell, an ejection pin, and a tail handle;

the shell is a pen shell structure of the lancing device, an ejection chamber is arranged inside the shell, and a lancing end face is provided at the front end of the shell;

the ejection pin is an ejection component capable of installing a lancet, the ejection pin is located in the ejection chamber, an active impact surface is set at the rear of the ejection pin to adjust puncture depth, and the active impact surface is facing towards the front of the lancing device;

the tail handle is a handle set at the tail of the lancing device to drive the ejection pin to be loaded;

wherein the tail handle is sleeved and connected relative to the shell, the tail handle is configured to rotate relative to the shell in a circumferential direction of the lancing device, and the tail handle is configured to slide relative to the shell in an axial direction of the lancing device at the same time;

between the tail handle and the shell, one of the tail handle and the shell is equipped with an axial limit surface, the other of the tail handle and the shell is equipped with a limit action part, and the axial limit surface is configured to contact the limit action part to limit the position of the tail handle relative to the shell to slide forward in an axial direction;

a passive impact surface is arranged corresponding to the active impact surface for both adjusting puncture depth and loading, the passive impact surface is directly or indirectly formed by a spiral action surface on the tail handle, rotating the tail handle is configured to change the position of the impact point on the passive impact surface in the axial direction of the lancing device;

in a use state, when the tail handle is rotated, the tail handle drives the position of the impact point on the passive impact surface to change in the axial direction of the lancing device, thereby changing the distance between the lancing end face and the impact point on the passive impact surface in the axial direction of the lancing device, thereby adjusting the lancet tip puncture depth;

when the tail handle is pulled backward, the tail handle forces the passive impact surface to contact the active impact surface at the rear of the ejection pin, and drives the ejection pin to move backward relative to the shell, until the ejection pin is loaded and locked;

the tail handle is designed to form a composite mating section with a housing of the shell, and at the composite mating section, one of the tail handle and the housing is provided with a plurality of guide grooves, and the other of the tail handle and the housing is provided with a guide block;

a length direction of the plurality of guide grooves is parallel to the axial direction of the lancing device, each guide groove of the plurality of guide grooves is spaced apart from each other along the circumferential direction of the lancing device;

at the composite mating section, the guide block and the plurality of guide grooves are configured to have a non-mating working state and a mating working state;

in the non-mating working state, the guide block and the plurality of guide grooves are staggered in the axial direction of the lancing device, such that the tail handle rotates relative to the housing in the circumferential direction of the landing device, and in the mating working state, the guide block and the plurality of guide grooves overlap each other in the axial direction of the lancing device, such that the tail handle slides relative to the housing in the axial direction of the lancing device.

2. The lancing device according to claim 1, wherein the passive impact surface is directly formed by the spiral action surface on the tail handle, and a sleeve structure is arranged on the tail handle, the sleeve structure is provided with an inner end face which is facing towards the rear of the lancing device, and the spiral action surface is a spiral step surface or a spiral surface or an inclined surface, the spiral step surface or spiral surface or inclined surface is directly arranged on the inner end face of the sleeve structure of the tail handle.

3. The lancing device according to claim 2, wherein the sleeve structure of the tail handle is composed of an outer sleeve and an inner sleeve; in an assembly state, the inner sleeve is fixed on the inner side of the front end of the outer sleeve, and the spiral step surface or spiral surface or inclined surface is directly arranged on the end face of the inner sleeve which is facing the rear of the lancing device.

4. The lancing device according to claim 3, wherein the outer edge of the inner sleeve is equipped with a positioning boss, and a positioning groove is arranged on the inner edge of the outer sleeve corresponding to the position of the positioning boss;

in the assembly state, the positioning boss on the inner sleeve fits with the positioning groove on the outer sleeve, to limit free degree of circumferential rotation of the inner sleeve relative to the outer sleeve;

the outer edge of the inner sleeve is equipped with a positioning convex rib, the positioning convex rib is perpendicular or at an angle to the axis of the lancing device; the inner edge of the outer sleeve is equipped with a positioning snap corresponding to the positioning convex rib;

in the assembly state, the positioning convex rib on the inner sleeve fits with the positioning snap on the outer sleeve, to limit free degree of axial movement of the inner sleeve relative to the outer sleeve.

5. The lancing device according to claim 1, wherein the passive impact surface is indirectly formed by the spiral action surface on the tail handle, a sliding sleeve is provided for the tail handle, the sliding sleeve is positioned and connected relative to the shell in a circumferential direction of the lancing device, and the sliding sleeve is connected in an axial direction of the lancing device at the same time;

the tail handle is connected to the sliding sleeve through a screw pair, constituting a sliding sleeve axial movement mechanism which is adjusted by the rotation of the tail handle;

the passive impact surface is the inner end face of the sliding sleeve, and the spiral action surface is the screw pair.

6. The lancing device according to claim 5, wherein the screw pair is formed by the cooperation of a spiral groove and a driving block;

between the spiral groove and the driving block, one of the spiral groove and the driving block is located on the tail handle, and the other of the spiral groove and the driving block is located on the sliding sleeve.

7. The lancing device according to claim 5, wherein the screw pair is formed by the cooperation of an external thread and an internal thread;

between the external thread and the internal thread, one of the external thread and the internal thread is located on the tail handle, and the other of the external thread and the internal thread is located on the sliding sleeve.

8. The lancing device according to claim 1, wherein a return spring is provided for the tail handle, and the return spring acts on the return direction of the tail handle;

in the initial assembly state, under an action of the return spring, the axial limit surface between the tail handle and the shell is configured to contact the limit action part, placing the tail handle in a front limit position relative to the shell;

after pulling the tail handle backward for loading, releasing the tail handle and under the elastic force of the return spring, the tail handle moves axially forward relative to the shell, and stops until the tail handle returns to the front limit position again.

9. The lancing device according to claim 1, wherein the tail handle is equipped with a rotating positioning structure in a circumferential direction of the lancing device relative to the shell, the rotating positioning structure is composed of a rotating positioning groove and a rotating positioning block in coordination;

between the rotating positioning groove and the rotating positioning block, one of the rotating positioning groove and the rotating positioning block is located on the tail handle, and the other of the rotating positioning groove and the rotating positioning block is located on the shell or on a component fixedly connected to the shell, wherein, the length direction of the rotating positioning groove is parallel to the axis of the lancing device, and the rotating positioning groove is disposed at an interval in the circumferential direction of the lancing device.

* * * * *